(12) United States Patent
Desrochers et al.

(10) Patent No.: US 7,360,461 B2
(45) Date of Patent: Apr. 22, 2008

(54) AIR MONITORING SYSTEM HAVING TUBING WITH AN ELECTRICALLY CONDUCTIVE INNER SURFACE FOR TRANSPORTING AIR SAMPLES

(75) Inventors: Eric M. Desrochers, Millis, MA (US); Gordon P. Sharp, Newton, MA (US); David L. Farrington, Boston, MA (US); Martin D. Flansbury, Newburyport, MA (US)

(73) Assignee: Aircuity, Inc., Newton, MA (US)

( * ) Notice: Subject to any disclaimer, the term of this patent is extended or adjusted under 35 U.S.C. 154(b) by 127 days.

(21) Appl. No.: 11/149,941

(22) Filed: Jun. 10, 2005

(65) Prior Publication Data

US 2006/0060004 A1    Mar. 23, 2006

Related U.S. Application Data

(63) Continuation-in-part of application No. 10/948,767, filed on Sep. 23, 2004, now Pat. No. 7,216,556.

(51) Int. Cl.
*G01N 35/08* (2006.01)
(52) U.S. Cl. .................. 73/864.81; 73/863.71
(58) Field of Classification Search ............. 73/863.71, 73/864.81
See application file for complete search history.

(56) References Cited

U.S. PATENT DOCUMENTS

| | | |
|---|---|---|
| 3,390,704 A | 7/1968 | Woodell |
| 3,898,369 A | 8/1975 | Clabbum |
| 4,156,127 A | 5/1979 | Sako et al. |
| 4,733,800 A | 3/1988 | Bjorkengren et al. |
| 4,900,383 A | 2/1990 | Dursch et al. |
| 5,412,975 A | 5/1995 | Raabe et al. |
| 5,476,121 A | 12/1995 | Yoshikawa et al. |
| 5,490,542 A | 2/1996 | Iorio et al. |
| 5,922,976 A | 7/1999 | Russell et al. |
| 6,125,710 A | 10/2000 | Sharp |
| 6,367,510 B1* | 4/2002 | Carlson ...................... 138/121 |
| 6,374,862 B1 | 4/2002 | Schwert |
| 6,425,297 B1 | 7/2002 | Sharp |
| 2002/0106470 A1* | 8/2002 | Merziger et al. ........ 428/36.91 |
| 2004/0071908 A1 | 4/2004 | Suzuki et al. |
| 2004/0238797 A1* | 12/2004 | Okada et al. ............... 252/500 |
| 2005/0011572 A1* | 1/2005 | Belcher ...................... 138/137 |

FOREIGN PATENT DOCUMENTS

DE    1092109    1/1954

(Continued)

OTHER PUBLICATIONS

PCT/US2005/033727 International Search Report dated Dec. 14, 2005.

(Continued)

*Primary Examiner*—Hezron Williams
*Assistant Examiner*—Paul M West
(74) *Attorney, Agent, or Firm*—Daly, Crowley, Mofford & Durkee, LLP

(57) ABSTRACT

An air monitoring system includes a tubing having an electrically conductive inner surface. In one embodiment, the liner includes carbon based materials, such as for example carbon nanotubes. In another embodiment, a conductive layer is adhered to a substrate.

23 Claims, 16 Drawing Sheets

FOREIGN PATENT DOCUMENTS

| | | |
|---|---|---|
| DE | 1.092.109 | 4/1955 |
| WO | WO 2006/034303 A1 | 3/2006 |

OTHER PUBLICATIONS

Daniel T. Colbert, Single-Wall Nanotubes: A New Option For Conductive Plastics and Engineering Polymers, Jan./Feb. 2003, pp. 1-7.

PCT/US2006/021218 International Search Report dated Oct. 31, 2006.

Polygraf Products, Inc., believe to be printed on or about May/Jun. 2005, pp. 1-6.

Modern Dispersions, Inc., Thermoplastics Compounding, believe to have been printed out from internet website on or about May/Jun. 2005pp. 1-6.

Texioc, Design & Manufacture, believe to be printed out from internet website on or about May/Jun. 2005, pp. 1-2.

Brian E. Callen, PH.D., James Mah, Practical Considerations For Loading Conductive Fillers Into Shielding Elastomers, 2002, pp. 130-137.

Cole Palmer Catalog —Technical Information, Physical Properties of Plastics, believe to be printed out from internet website on or about May/Jun. 2005, 1 page.

Tubing Selection Guide, believe to be printed out from internet website on or about May/Jun. 2005, p. 2042.

Sampling Systems, Edge Tech Dew Point Hygrometer Sampling Systems, believe to be printed out from internet website on or about May/Jun. 2005, pp. 1-2.

Chemical Resistance of Thermoplastics Used In Dual Laminate Constructions, believe to be printed out from internet website on or about May/Jun. 2005, pp. 1-143.

Suzanne Shelley, Carbon Nanotubes: A Small-Scale Wonder, Feb. 2003, pp. 1-2.

Hyperion Catalysis International, INC., Preservation of Physical Properties in Molded Parts Using Compounds with FIBRIL Nanotubes, pp. 1-4, Aug. 2002, Cambridge Massachusetts.

Andrew Rich, Patrick Collins, John Hagerstrom, Nanotubes for Conductive Plastics Move to the Next Performance Level, pp. 1-7, 2002, Society of Automotive Engineers, Inc.

Saint-Gobain Performance Plastics, Engineering Section, believe to be printed out from internet website on or about May/Jun. 2005, 1 page.

Elsevier Advanced Technology, Single-Wall Nanotubes A New Option for Conductive Plastics And Engineering Polymers, 2002, pp. 1-9.

Elsevier Advanced Technology, New Carbon Blacks Offer Electrostatic Discharge & Improved Mechanical Properties, Apr. 8, 2003, pp. 1-8.

Hydex A Registered Trademark of A.L. Hyde Company, Machinist-Materials, Plastics Characteristics Comparison Table, believe to be printed out from Internet website on or about May/Jun. 2005, pp. 1-13.

Particle Loss in Transport Tubing, PMS Application Note 15, Particle Measuring Systems, Inc., Boulder, CO, 1997.

Table Z-1 Limits for Air Contaminants, OSHA Regulations Standard 1910.1000 Table Z-1.

Gregory Yoder, Laser-Based Analysis of Ambient Air Particles, Journal of Undergraduate Research, University of Florida, Jun. 2001.

M. Shapiro and S. Lekhtmakher, Measurement of Aerosol Effective Transport Coefficients in Cylindrical Tubes, J Aerosol Sci. vol. 30, No. 8, 1999.

Harold Kinley, C.E.T., Locating Cable Faults With the Time Domain Reflectometer, Mobile Radio Technology, Nov. 1997.

David B. Kittleson, Ph.D., Megan Arnold and Winthrop F. Watts, Jr., Ph.D., Review of Diesel Particulate Matter Sampling Methods, Final Report, University of Minnesota Department of Mechanical Engineering Center for Diesel Research, Jan. 1999.

David B. Kittleson, Ph.D., Megan Arnold and Winthrop F. Watts, Jr., Ph.D., Review of Diesel Particulate Matter Sampling Methods, Report #2, University of Minnesota Department of Mechanical Engineering Center for Diesel Research, Jul. 1998.

H. Wirzberger, S. Lekhtmakher, M. Shapiro and V. Dudko, Prevention of Particle Deposition by Means of Heating the Deposition Surface, J. Aerosol Science vol. 28, Suppl 1, 1997, pp. S83-S84.

* cited by examiner

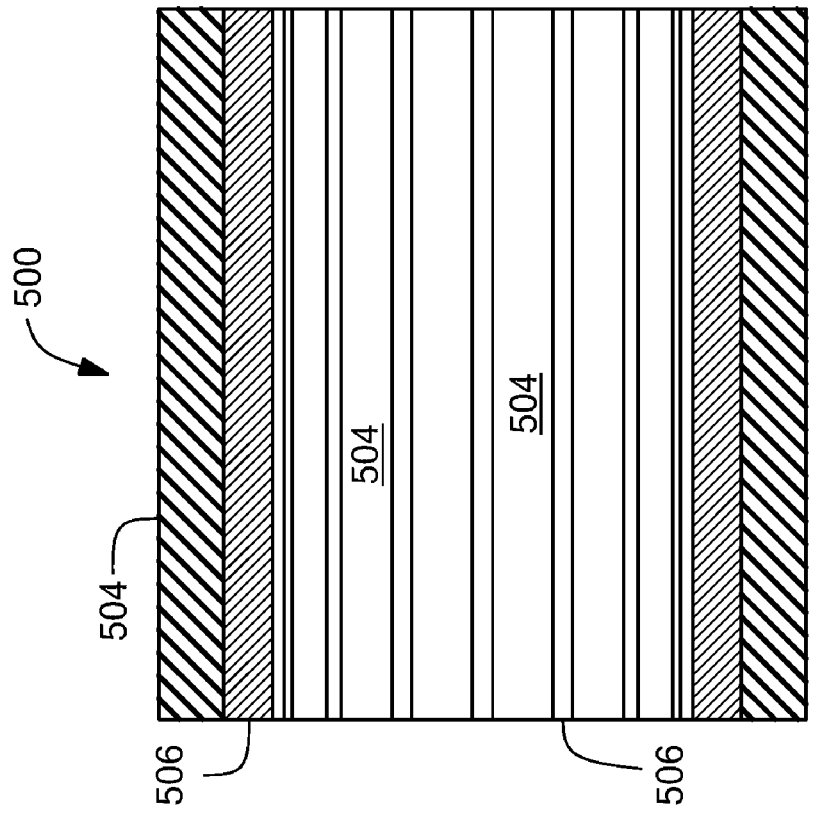
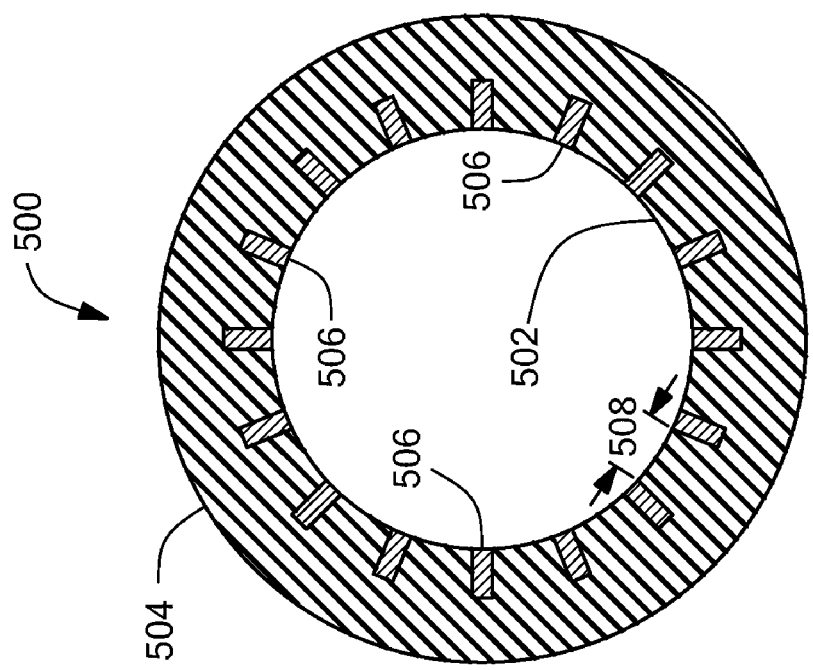
FIG. 5B
FIG. 5A

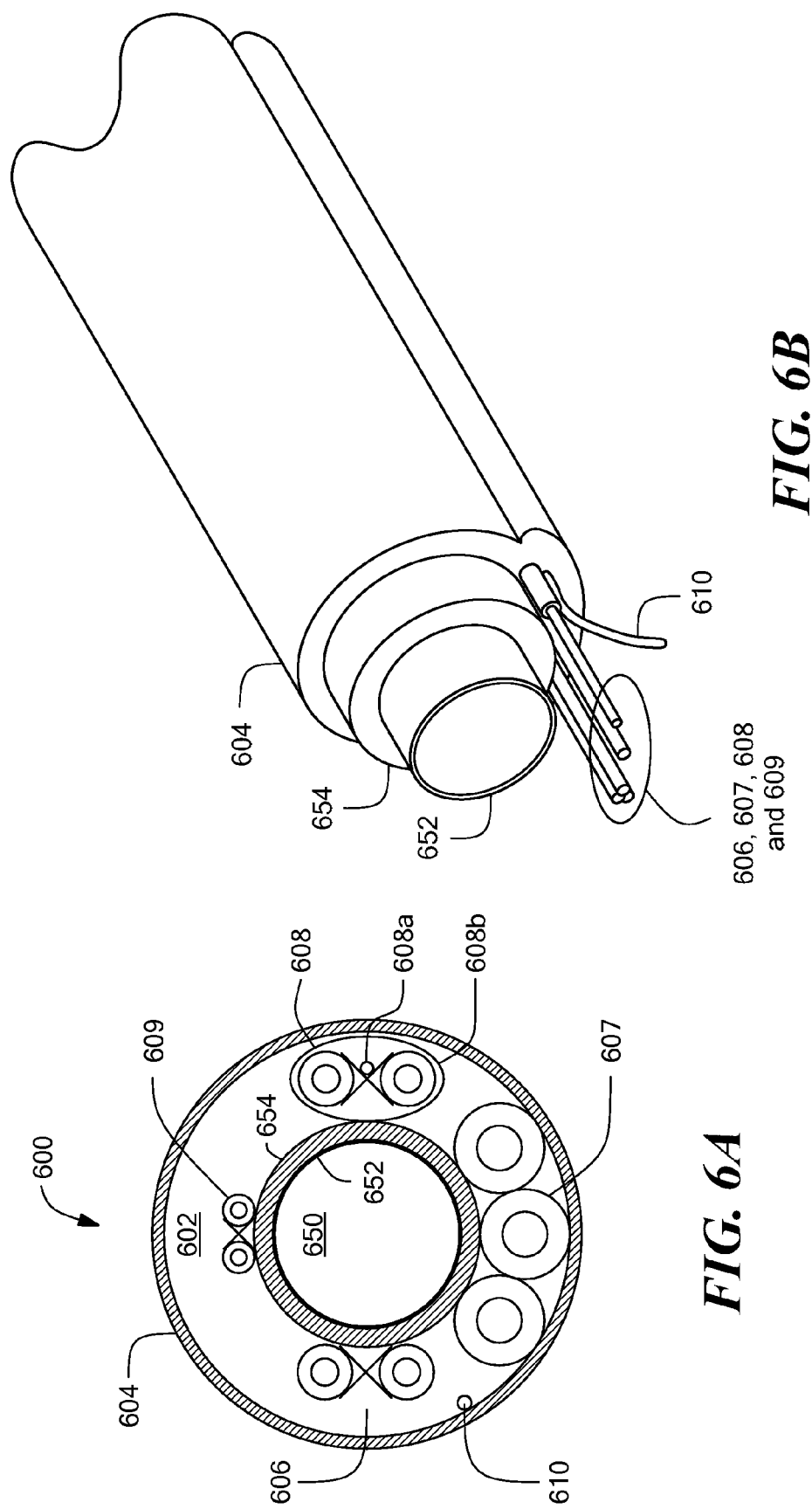

AIR MONITORING SYSTEM HAVING TUBING WITH AN ELECTRICALLY CONDUCTIVE INNER SURFACE FOR TRANSPORTING AIR SAMPLES

CROSS REFERENCE TO RELATED APPLICATIONS

The present application is a continuation-in-part of U.S. patent application Ser. No. 10/948,767, filed on Sep. 23, 2004, which is incorporated herein by reference.

STATEMENT REGARDING FEDERALLY SPONSORED RESEARCH

Not Applicable.

FIELD OF THE INVENTION

The present invention relates generally to air sampling and, more particularly, to systems for measuring air characteristics.

BACKGROUND OF THE INVENTION

As is known in the art, there are various applications where air is transported through a tube or pipe for sampling or measurement purposes. For example, an air quality measurement system may have remotely located sensors instead of at the sensed environment. In addition, a sensor may be used to sense several locations. For such systems, multiple tubes may be used to bring air samples from multiple locations to a centralized sensor(s). Centrally located air switches and/or solenoid valves may be used in these approaches to sequentially switch the air from these locations through the different tubes to the sensor to measure the air from multiple remote locations. These octopus-like or star-configured systems use considerable amounts of tubing. Another multiple-location sampling system known as a networked air sampling system uses a central 'backbone' tube with branches extending to various locations. Air solenoids can be remotely located proximate the multiple sampling locations. Air sampling systems can include remote and/or multiple-location air sampling through a tube or pipe for sampling locations in a building, outdoor air or ambient sampling, and sampling in smokestacks and exhaust air stacks. An exemplary air sampling system is described in U.S. Pat. No. 6,125,710, which is incorporated herein by reference.

As known in the art, air sampling systems can use various types of tubing to transmit air samples or 'packets' to the appropriate sensor. One type of tubing is TEFLON tubing. However, TEFLON tubing is relatively expensive and has certain undesirable particle transport characteristics, such that it is a poor conductor and tends to establish a charge as an air sample passes through a tube of such material resulting in enhanced electrostatic deposition of particulate matter from the flow stream. Low or High Density Polyethylene (LDPE or HDPE) tubing, which is less expensive than TEFLON tubing, has been used with limited success. Although good for indoor air quality CO2 sensing, the LDPE or HDPE tubing absorbs and desorbs volatile organic compounds (VOCs) leading to inaccurate sensing results. This type of tubing is also poor for particle sensing applications since the plastic is an electrically poor conductor and can hold a charge resulting in relatively poor transport properties as a result of electrostatic deposition.

Some types of plastic tubing can be used for transporting particles. For example, one type of plastic tubing is known as "Bev-A-Line XX" tubing made by Thermoplastic Processes, Inc. of Stirling, N.J., can be used to perform air sampling with particle transport efficiencies that are an improvement over that possible with polyethylene tubing. However, "Bev-A-Line XX" tubing is quite expensive and absorbs VOCs. Similarly, silicone tubing is sometimes impregnated with large amounts of carbon black (a powdered form of highly dispersed elemental carbon) to create conductive silicone tubing for transporting particles. For example, TSI, Inc., manufactures various sized conductive silicone tubing such as their part number 3001789, which has an inner diameter of 0.31 inches and an outer diameter of 0.375 inches. This tubing is typically used in aerosol research to transport aerosol particles to portable instruments. However, conductive silicone tubing also absorbs and desorbs VOCs. Also silicone specifically attacks and compromises the operation of metal oxide semiconductor TVOC (Total Volatile Organic Compound) sensors of the type that are commonly used to measure the level of VOCs in air samples.

While certain metal tubing may have desirable properties for transporting air samples, known metal tubing options may have certain drawbacks. For example, some metal tubing is rigid rendering it quite expensive to install, because of the labor involved with that process. While other metal tubing may be deformable so as to facilitate installation, the metal characteristics are not well suited for air sampling applications. One known tubing manufactured by Synflex of Mantua Ohio, a division of Saint-Gobain Performance Plastics, includes an aluminum-lined polyethylene tube (Type 1300 Synflex, formerly known as Dekabon) to provide a stronger plastic tube with a higher burst resistance and pressure rating for high pressure pneumatic applications. The internal aluminum liner is also coated with an adhesive to help attach the aluminum inner tube together with the outer plastic jacket. It also has a plastic coating on the inner portion of the tube for added chemical resistance. However, such a tubing configuration is undesirable for use as an air-sampling medium. The inner coating attracts and traps particles and absorbs VOCs. In addition, even if the coating was not used the aluminum is reactive with many indoor contaminants. Due to its reactive nature, the aluminum tubing would not give accurate and reliable performance as an air sampling tubing. Further, the aluminum surface has an affinity to oxidize over time as it is exposed to ambient air conditions. The surface oxidation increases the roughness of the inside of the tube and can result in the release of particulate matter in the form of aluminum oxide, which can have a non-negligible impact on a given concentration of particulate matter being sampled via transport through the tubing.

SUMMARY OF THE INVENTION

The present invention provides a tubing structure that is well suited for transporting air samples in an air monitoring system. In an exemplary embodiment, the tubing includes a metallic layer, which can be provided as stainless steel, to efficiently transport particulate matter with minimal absorption and off-gassing. The tubing can include a jacket such that the overall tubing structure can be bent, cut, and joined in a manner that is similar to that of conventional tubing.

In one aspect of the invention, a method of transporting an air sample can include one or more of the following features: obtaining an air sample from a first location, transporting the air sample to a second location in a tubing including an electrically conductive layer having carbon nanotubes or carbon nanofibers, and measuring at least one characteristic of the air sample using a sensor. The method can further include one or more features including: an inner layer encompasses the entire thickness of the tubing wall; wherein the inner layer includes a host material loaded with between one and six percent by weight carbon nanotubes; wherein the host material includes one or more of fluoropolymer resin plastics such as PTFE, FEP, PFA, PEEK, EFTE, CTFE, ECTFE, MFA, THV, and PEI; wherein the tubing includes an outer layer that does not contain substantive amounts of carbon single wall nanotubes; and wherein the sensor suite measures some level of information about the amount of particles in the air sample along with one of either a measure of VOCs, dew point, or carbon dioxide levels.

In another aspect of the invention, an air sampling system includes a sensor suite, air intake valves for switching air samples, and tubing coupled to the air intake valves and a series of termination points from which air samples are obtained and transported via the tubing to the sensor suite, wherein at least a portion of the tubing includes an electrically conductive layer having carbon nanotubes. The system can further include one or more of: wherein the tubing includes no outer layer, only an inner layer encompasses the entire thickness of the tubing wall; wherein the inner layer includes a host material loaded with between about one and six percent by weight carbon nanotubes; wherein the host material includes one or more of fluoropolymer resin plastics such as PTFE, FEP, PFA, PEEK, EFTE, CTFE, ECTFE, MFA, THV, and PEI; wherein the tubing includes an outer layer that does not contain substantive amounts of carbon nanotubes; wherein the inner layer has a thickness in a range from about 0.005 inch to about 0.03 inch; and wherein the sensor suite measures some level of information about the amount of particles in the air sample along with one of either a measure of VOCs, dew point temperature (or other psychrometric property), or carbon dioxide levels.

In another aspect of the invention, an air sampling system includes a sensor suite for measuring two or more air parameters; wherein one of those parameters could be particles and another parameter of the air sample could, for example, be VOCs, humidity, carbon dioxide, ozone, carbon monoxide air PH, ammonia, refrigerants, formaldehyde, nitrous oxide (N2O), NO, NO2, SO, SO2, mold spores, or another air parameter. Also included in the system are air intake valves for switching air samples, and tubing coupled to the air intake valves and a series of termination points from which air samples are obtained and transported via the tubing to the sensor suite, wherein at least a portion of the tubing includes an electrically conductive layer containing a carbon based material such as for example: carbon single wall-nanotubes, carbon multi-wall nanotubes, carbon nanofibers, carbon fibers, graphite, or carbon black. The system can further include one or more of: wherein the tubing includes no outer layer, only an inner layer encompasses the entire thickness of the tubing wall; wherein the inner layer includes a host material loaded with the carbon based material; wherein the tubing includes a nonconductive outer layer that does not contain substantive amounts of carbon based material; wherein the host material includes one or more of fluoropolymer resin plastics such as PTFE, FEP, PFA, PEEK, EFTE, CTFE, ECTFE, MFA, THV, and PEI.

In a further aspect of the invention, a method of transporting an air sample includes obtaining an air sample from a first location, transporting the air sample to a second location in a tubing including an electrically conductive metal liner adhered to a substrate, and measuring at least one characteristic of the air sample using a sensor. The method can further include one or more of: wherein the metal liner is metallized with stainless steel; wherein the tubing includes an outer jacket; wherein the metal liner includes stainless steel foil; wherein the metal liner includes aluminum foil; wherein the aluminum foil includes a surface of anhydrous aluminum oxide; wherein the metal liner includes a metallized layer; wherein the metal liner includes nickel-plated copper foil; wherein the metal liner includes a foil layer deposited directly onto the substrate; and wherein the substrate is made of polyamide film (such as Kapton®).

In another aspect of the invention, an air sampling system, includes a sensor suite, air intake valves for switching air samples, and tubing coupled to the air intake valves and a plurality of termination points from which air samples are obtained and transported via the tubing to the sensor suite, wherein the tubing includes an electrically conductive metal liner adhered to a substrate. The system can include one or more of the features described above.

BRIEF DESCRIPTION OF THE DRAWINGS

The invention will be more fully understood from the following detailed description taken in conjunction with the accompanying drawings, in which:

FIG. 5A is a width cross-sectional view of another embodiment of a composite tubing in accordance with the present invention;

FIG. 5B is a length cross-sectional view of the tubing of FIG. 5A;

FIG. 6A is a cross-sectional view of a structured cable assembly including a composite tubing in accordance with the present invention;

FIG. 6B is an isometric view of the structured cable assembly of FIG. 6A.

DETAILED DESCRIPTION OF THE INVENTION

Figure 1:
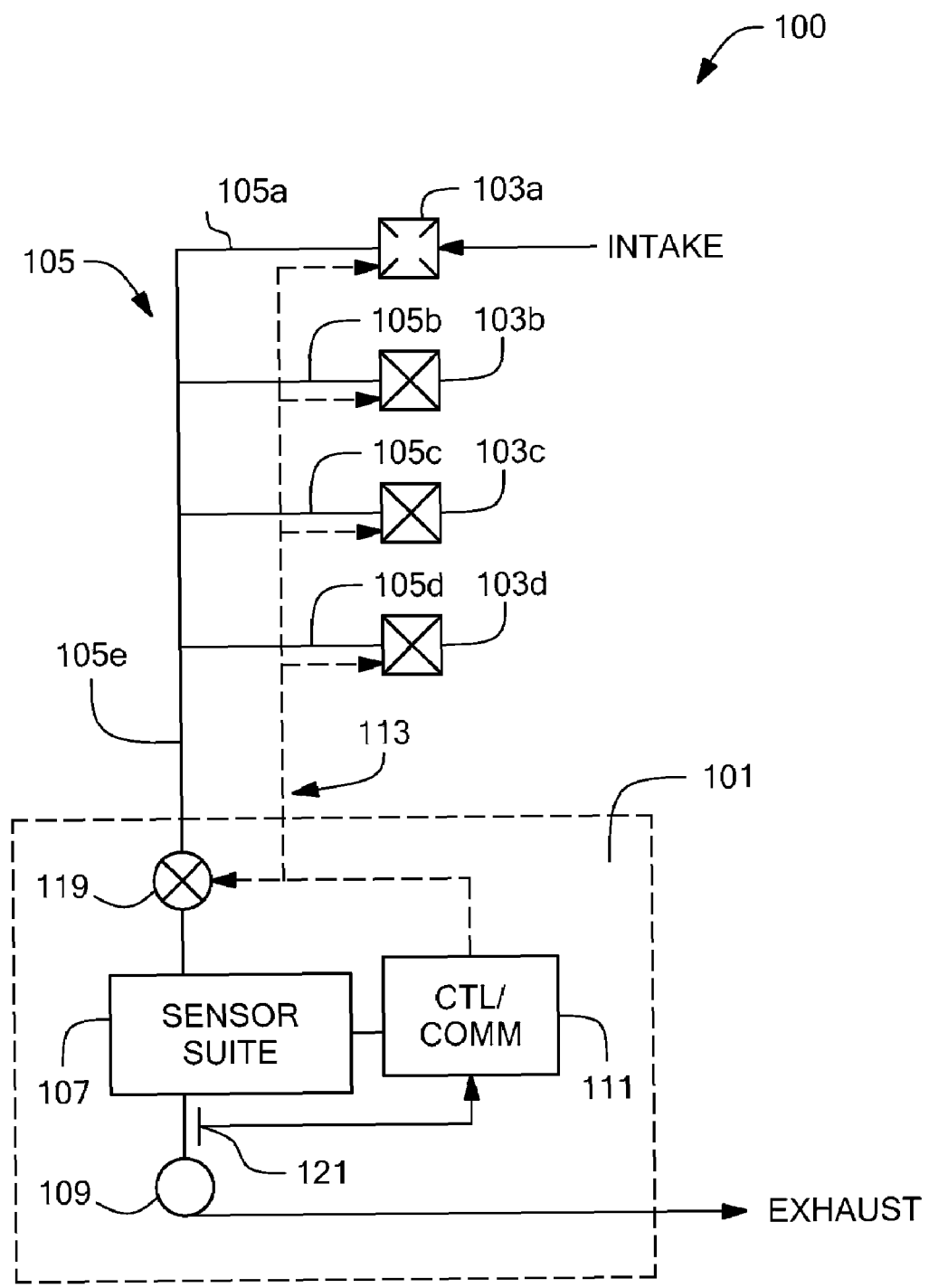
FIG. 1 is a block diagram of an air sampling system having tubing in accordance with the present invention.

FIG. 1 shows an exemplary air monitoring system 100 having tubing in accordance with the present invention to provide optimal transport of air samples. In general, the system 100 transports air samples or packets from a first location, such as a room, to a second location at which one or more sensors are located. The sensors measure various characteristics of the air, such as CO, CO2, TVOCs, dew point temperature and/or humidity, ozone, air PH, one or more of other gases or vapors such as, Nitrous oxide, SO2, SO, NO2, NO, ammonia, methane, hydrogen sulfide, refrigerants, and formaldehyde. Additionally, light obscuration sensors can be used to measure the amount of particulate matter in a given size range or a particle counter sensor can be used to provide information such as a count per unit of sample volume of small particles ranging from about 0.3 uM to about 2.5 uM, a count per unit of sample volume of large particles ranging from 2.5 uM to 10 uM, a count per unit of sample volume of particles of other desired size ranges, and a count per unit of sample volume of ultra fine particles ranging from about 0.02 uM to 1 uM. The inventive tubing includes a metallic inner layer and an optional jacket layer. The metallic inner layer, which can be formed from stainless steel, provides efficient transport of particulate matter in the air samples with relatively low absorption and off-gassing for accurate air quality monitoring.

Before describing the inventive composite tubing in detail, an exemplary air sampling system as described in U.S. Pat. No. 6,125,710 is briefly discussed in which the tubing can be used. The system 100 of FIG. 1 includes a central sensing and control system 101 connected to a plurality of air intake valves 103*a*-103*d* through a network of composite tubing 105. The network of tubing 105 has a backbone section 105*e* and branches 105*a*-105*d* corresponding to and connected to respective air intake valves 103*a*-103*d*. The central sensing and control system 101 includes a sensor suite 107 connected to an end of tubing backbone section 105*e*, an air pump 109 connected to the sensor suite 107 to draw air through the system, and a control and communications unit 111 for controlling operation of the sensor suite 107, the air intake valves 103*a*-103*d*, and the air pump 109, as well as communicating with the sensor suite 107 and external equipment. The control and communications unit 111 can control the various elements through a fiber optic, electronic or pneumatic control network 113, including network device adapters 115 (FIG. 1A) for input/output functions and, optionally, a number of control network routers 117 for controlling communication within the control network.

Figure 1A:
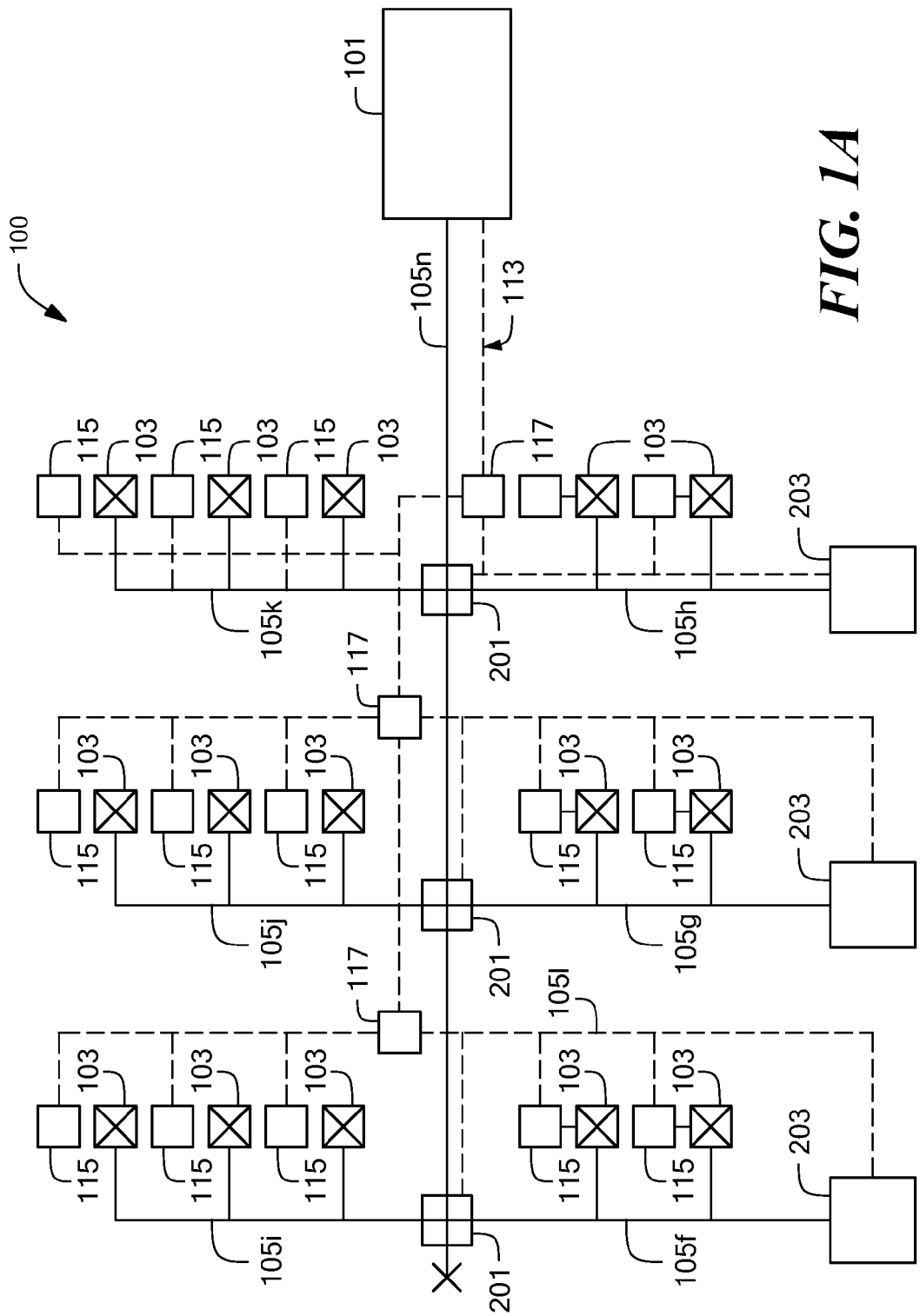
FIG. 1A is a block diagram showing further details of the system of FIG. 1.

Alternatively, the network device adapters 115 and control network routers 117 of FIG. 1A can be omitted, with the control and communications unit 111 either communicating directly with the device adapters 115 or directly with the controlled elements, such as valves 103. A digital communications network can be employed as part of the control network 113.

While the air pump 109 draws air through the system, the control and communications unit 111 operates the air intake valves 103*a*-103*d* in a sequence, so that each valve (e.g. valve 103*a*) is open for a time while the others (e.g. valves 103*b*-103*d*) are closed, thus drawing an air sample into the system from a sample site at which the open valve (e.g. valve 103*a*) is located. In the configuration of FIG. 1, air samples from a plurality of valves (e.g., 103*a*-103*d*) are drawn in the control sensing and control system 101 through a single backbone section 105*e*. Sensor suite 107 thus has only one inlet port to which backbone section of tubing 105*e* is connected.

The sensor suite 107 measures various parameters of the air sample passing through the sensor suite. Individual sensors within the sensor suite 107 may be arranged to receive air from the inlet either in series or in parallel, depending upon the flow rate requirements, pressure requirements and effects of the sensors on the sample chemistry or other properties. In a series connection, the air sample passes through each series-connected sensor in sequence, while in a parallel connection the air sample passes through each parallel-connected sensor at the same time. The control and communications unit 111 reads the measurements made by the sensor suite 107 and communicates the readings to external equipment (not shown) such as building air flow controls, fume hood controllers, etc. Either the control and communications unit 111 or the external equipment may use the data collected in a variety of ways, including, but not limited to passive data collecting, activating alarm mechanisms under specified conditions, activating safety mechanisms under specified conditions, and changing local or overall air flow parameters by issuing commands to the air flow control equipment.

According to a first technique, each air intake valve 103*a*-103*d* is opened in a sequence 103*d*→103*c*→103*b*→103*a*, drawing four corresponding samples D, C, B and A into the sensor unit 107. The time and duration of opening each valve is selected to be long enough for a stable sample larger than the inter-sample interface volume to be obtained through the air intake valve 103*a*-103*d*, thus ensuring a good sample reaching the sensor unit 107 regardless of whether there is a next upstream air intake valve 103*a*-103*d* to be opened in the sequence. The time for sample A to travel from air intake valve 103*a* to the sensor unit 107, TA, is assumed to be known, for example by prior measurement. When the time TA has passed from the opening of air intake valve 103*a*, plus an additional time necessary to move the portion of the sample A in the sensor unit 107 beyond any interface volume between the sample A and an adjacent prior sample, then the sensor unit 107 performs the measurements for which it is equipped.

According to a second technique, each air intake valve 103*a*-103*d* is opened in a sequence 103*a*→103*b*→103*c*→103*d*, drawing four corresponding samples A, B, C and D into the sensor unit 107. Also as described above, each valve is held open for a time sufficient for a stable sample to be drawn past the next downstream air intake valve to be opened in the sequence or, as is the case for valve 103d a time sufficient for a stable sample to be delivered to sensor unit 107, following which 103d will be closed and valve 103a will be opened to start the sequence over again. The time is again selected to be sufficient for a stable sample, larger than the inter-sample interface volume, to be obtained through the air intake valve 103a-103d, thus ensuring a good sample reaching the sensor unit 107 regardless of whether there is a next downstream air intake valve 103a-103d to be opened in the sequence. As above, measurements may be timed to occur at times defined by the known travel times TA-TD after each valve 103a-103d has opened and the interface volume transit time through the sensor unit 107.

Instead of timing, a third technique relies on measuring the samples A-D which are large enough to produce stable measurements over a substantial period of time ranging from a few milliseconds to a few seconds. The sensor unit 107 is continually operated and monitored to determine the dynamic characteristics of the air stream flowing past the sensors contained therein. During times when the measurements are changing, the inter-sample interface is passing through the sensor unit 107. During times when the measurements are substantially stable, the useful stable portion of a sample is passing through the sensor unit 107. The sensor unit 107 may be connected to a control system 111 that uses past measurement data to estimate when each future sample will be valid.

FIG. 1A shows further aspects of an air monitoring system, such as the system 100 of FIG. 1. The system 100 includes the central sensing and control unit 101, as described in above, connected through tubing network 105 to a plurality of air intake valves 103, as now described. Several subnetworks are defined by backbone sections 105f-105k each connected to a main backbone including segments 105e-105n of tubing network 105 through routers 201. The routers 201 are air flow switches, for example, controlled electronically or pneumatically by control and communication unit 111 of the central sensing and control unit 101.

The system 100 can include distributed sourcing/sensing packages 203, connected to at least some branches (e.g. 105a-105c) of tubing 105. The distributed sourcing/sensing packages 203 may include one or more sensors and an air pump connected to draw air from the branch of tubing 105, through the sensors.

The system 100 provides significant flexibility and redundancy. By selectively setting the connections made by each of the routers 201 and by selectively opening one of the air intake valves 103, an air sample may be routed from any air intake valve 103 site to any sensor 101 or 203.

The present invention provides a tubing structure having an inner metallic layer, e.g., stainless steel, and an outer jacket that is composed at least in part of a non-metallic material, e.g., PVC, for optimal air transport that is useful in air sampling systems, such as the system described above, as well as other applications. Non-metallic materials may include either synthetic or non-synthetic materials. The inventive tubing is well suited for air sampling systems that pull air through a tube to measure the parameters of the air at a remote location. In general, the tubing includes an inner stainless steel liner and an optional outer plastic jacket.

In one embodiment, the tubing has certain mechanical properties that may be similar to conventional plastic tubing. For example, the inventive tubing can be installed throughout a structure with relative ease as the tubing can be pulled, bent, cut, joined, and otherwise manipulated. The installed cost of the inventive tubing is less than rigid stainless steel tube sections and coiled stainless steel tubing. In addition, due to the relatively low mass and greater flexibility of the tubing in relation to solid 304 stainless steel tubing, lighter duty fittings can be used to splice sections together during installation. Thus, lower cost quick-connect fittings, such as the John Guest Super Speedfit®, can be used. This is desirable over the use of relatively expensive Swagelok® type fittings, field threaded couplings, and welds, which are typically required to connect solid stainless steel pipe in order to provide a reliable connection.

Figure 2:
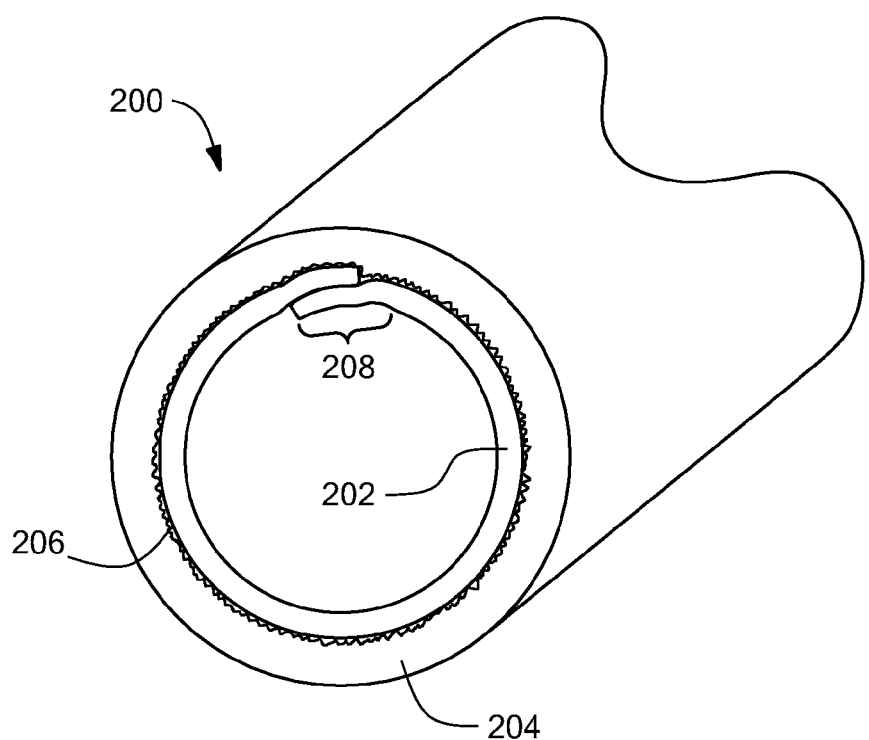
FIG. 2 is a schematic representation of composite tubing in accordance with the present invention.

FIG. 2 shows an exemplary composite tubing arrangement 200 including a metallic liner 202 covered by a jacket 204 of suitable material, which can be extruded over the liner. In an exemplary embodiment, the liner 202 is constructed of a ribbon of stainless steel that has been folded into a tubular form and the jacket is made of polyethylene. To improve adhesion of the stainless steel to the plastic jacket, an optional adhesive material, such as an ethylene copolymer or similar preferably heat-set material, may be used on the outer surface of the metallic liner 202 such that none of the adhesive material is present on the inside surface of the liner.

In one particular embodiment, the inner liner 202 is formed from 304 stainless steel to provide optimal properties for transporting most gaseous components (including VOCs) and particulate matter at the concentrations of interest for indoor air quality and other monitoring purposes. For example, the inventive tubing is suitable for transporting samples of various gases common within building environments having concentrations as low as several parts per billion (PPB). This is especially useful for monitoring substances which have low permissible exposure limits (PELs), such as Benzene, Arsine, Chlorine Dioxide, and most other substances listed, for example, under OSHA Regulations Standard 29 CFR, which is incorporated herein by reference. Further details of measuring air contaminants such as these are set forth in U.S. Pat. No. 6,609,967, which is incorporated herein by reference, describing the use of a multi-point sampling system to continuously monitor and validate air that is re-circulated from multiple locations within a building. The inventive tubing is particularly well suited for laboratory environments, such as wet chemistry labs, where any variety of potential contaminants may be present.

As is well known in the art, 304 stainless steel refers to a particular Chromium-Nickel austenitic alloy that is one of the most familiar and frequently used alloys in the stainless steel family. The metallic liner 202 is electrically conductive so as to prevent the accumulation of electrostatic charge on the inner surface, which helps to promote the efficient transport of particulate matter through the tube for air quality monitoring purposes. The metallic liner 202 also provides an interior surface having relatively low absorption and off-gassing properties.

It is understood that the metallic material used for the liner 202 can be selected based upon its properties with regards to the materials to be sampled through the tube for a particular application. Exemplary liner materials include various stainless steels including various austenitic, martensitic, and Ferritic grades, along with precipitation-hardened steels. In one particular embodiment, 304 stainless steel is used because of its corrosion and heat resistance properties and its good mechanical properties over a wide range of temperatures. In addition, other suitable metals (depending on the process used to form the liner) include but are not limited to bronze, gold, nickel, nickel alloys, titanium alloys, and electrically conductive conversion coated metals such as aluminum with a chromate coating.

In an exemplary embodiment, the jacket 204 is provided as polyethylene due to its ability to provide excellent crush resistance to the metal liner. However, other suitable materials include, but are not limited to, PVC (particularly one that is suitable for use in plenum environments, where that is a requirement), Teflon®, Mylar®, and various fluoroplastics (FEP, PFA, CTFE, ECTFE, ETFE). More generally, a broad variety of plastics may be used for the jacket material, based on the workability, weight, abrasion resistance, stiffness, and smoke and fire rating that is desired.

The composite tubing having a metallic liner 202 and plastic jacket 204 can be fabricated in a variety of ways using suitable materials. In the exemplary tubing 200 embodiment of FIG. 2, a stainless steel ribbon is formed into a tube with its edges overlapped in a first region 208 without any welding. The outer jacket 204, which can be formed from polyethylene, is then extruded over the stainless steel tube.

Alternatively, a stainless steel ribbon or tape is formed into a tube with the edges butted together and not overlapped. The seam of the stainless steel ribbon is continuously welded and the polyethylene outer jacket is extruded over it.

In one particular embodiment, the liner 202 is formed from 304 stainless steel ribbon having a thickness of 0.002 inch and a width of 1.0 inch. Depending on the parameters of the extrusion process involved in forming the outer jacket over the stainless steel liner, the stainless steel can be of any practical thickness ranging from, but not limited to, about 0.0005 inch to about 0.004 inch. In an illustrative embodiment, the outer diameter of the tube 200 is about ⅜ inch with an inner diameter of ¼ inch to 5/16 inch.

It is understood that various combinations of liner and jacket materials can be used to meet the needs of a particular application. For example, stainless steel may not be ideally suited for sampling halogenated hydrocarbons (such as ethylene dichloride, vinyl chloride, and ethylene dibromide), and other halogenated VOCs. These compounds used to be quite common in pesticides (e.g. chlordane and heptachlor), cleaning fluids (e.g. carbon tetrachloride), degreasers and paint solvents. The use of these compounds has been banned or discouraged in the United States because of their toxicity, so they are not found in indoor air as often as previously. However, they may still be present because old stocks might still be available and they may also still be in use in foreign countries. Where there is special interest in measuring this class of VOCs, the metallic liner 202 may be made of Gold, for example, as Gold is relatively chemically inert for these gaseous components. It is understood that the liner can include a Gold coating over another material.

The inventive tubing provides a metallic inner layer for optimal air transport properties as well as flexibility to facilitate installation within a building. Because of its flexibility, the cost of installing the inventive tubing can be significantly less than that of prior art tubing, such as rigid stainless steel tube. One factor affecting the flexibility of the tubing structure is the flexure modulus of the material(s) from which the tubing is made. It is well known that for a given geometry, a structure, such as a tube, becomes more flexible when made with materials having a low flexure modulus. As used herein, flexibility refers to the amount by which the tube will deflect as it is subject to a bending force.

Figure 2A:
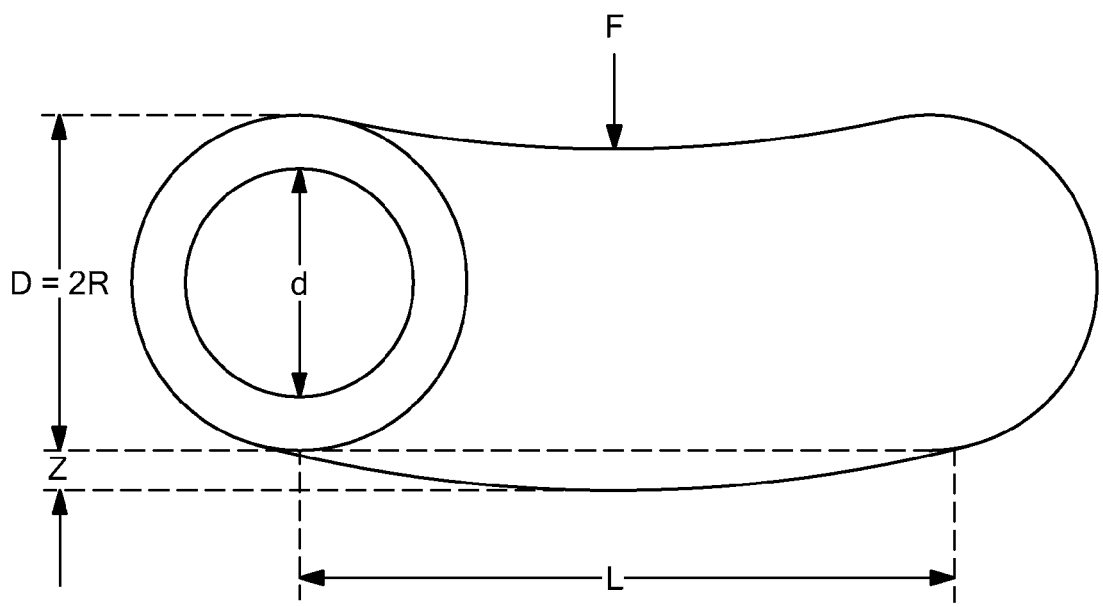
FIG. 2A is a schematic depiction of composite tubing having bending flexibility.

FIG. 2A shows how the inventive tubing will bend when suspended between two points separated by a distance L and a force F is applied for a tubing having an outer diameter D and an inner diameter d. For a given geometry (fixed values of L, D, and d) and the application of a predetermined force F, the amount of deflection Z (the tubing's flexibility) increases as the flexure modulus of the tubing material is decreased. Because the flexure modulus for 304 stainless steel is relatively high (approximately $28 \times 10^6$ psi, as opposed to about $0.5 \times 10^6$ psi for a relatively stiff PVC material that might be used in the tubing jacket), the application of some predetermined amount of force F on stainless steel tubing will deflect significantly less than the same tubing configuration made from a plastic material, for example. Because of the differences in flexure modulus, depending on the thickness of the metallized liner, the inventive tubing, which includes a non-metallic outer jacket, will be 50 to 100 times (or more) flexible than 304 stainless steel tubing. That is, the effective flexure modulus of the composite tubing (inner metallic layer and outer jacket) is approximately 50 to 100 times less than that of 304 stainless steel tubing. It is understood that this lesser flexure modulus as compared to 304 stainless steel tubing is applicable to the various exemplary inventive tubing embodiments shown and described herein.

FIG. 3 shows an exemplary embodiment of a composite tubing 300 in accordance with the present invention having a metallic material 302 applied to the inner surface of a tubing material substrate 304. The metallic material 302, which forms a liner for the tubing 300, may be a metallic paint, a deposited metal (utilizing any one of various known metal deposition techniques) or, a metallic insert or metal tube slipped into the substrate 304.

In one embodiment, the coating 302 on the inner surface of the substrate 304 can be applied by slitting a prefabricated length of tubing (e.g. polyethylene) along one radius, opening the tube to expose the inner surface, and applying a thin metallic film (such as stainless steel) by the vacuum vapor deposition technique. The tubing 300 is then resealed by ultrasonic welding providing, for example, a polyethylene or PVC tube with a thin-film stainless steel lining.

This tubing fabrication process yields an inner surface coating 302 that is more uniform than the liner surface of FIG. 2 and eliminates seams that can affect particle transport efficiency.

In another embodiment, instead of substrate 304 being a prefabricated length of tube, substrate 304 may be an extruded ribbon of jacket material, that is metallized to form coating 302. The metallized substrate is then rolled to form a tube 300 and its seam is sealed using ultrasonic welding techniques.

In another embodiment, a composite tubing is fabricated by applying a metal film as a polyethylene or PVC tubing is extruded. A relatively small metal vaporization probe is located near the extrusion die applying vaporized metal, such as stainless steel, to the inner surface of the tubing at it passes through the forming guides while maintaining a vacuum in the working area.

Figure 3A:
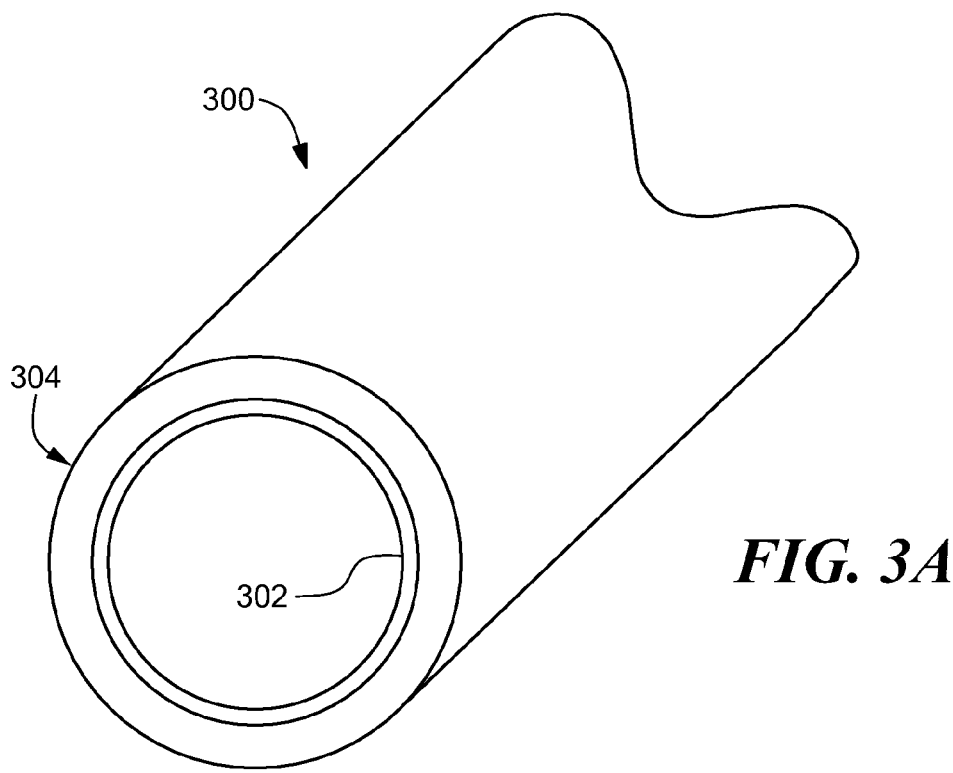
FIG. 3A is a schematic representation of a further embodiment of a composite tubing in accordance with the present invention.

In another embodiment shown in FIG. 3A, a tubing 300 includes a liner 302 formed from a material such as Mylar®, Teflon®, Kapton®, or some other suitable film, which is coated with metal, and adhered to the outer jacket 304 by way of a copolymer adhesive placed between the liner 302 and the outer jacket 304.

Figure 3B:
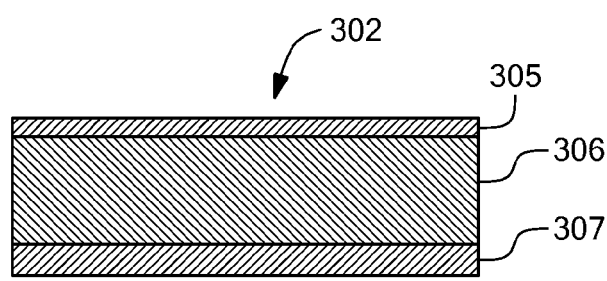
FIG. 3B is a cross-sectional view of an embodiment of a composite liner that may be used to line the tubing of FIG. 3A.

FIG. 3B shows an exaggerated cross sectional unfolded view of the composite liner 302 of FIG. 3A including a substrate 306 that is, using vapor deposition, sputtering, or other similar techniques of metal deposition known to those skilled in the art, deposited with a metallic layer 305 that comprises stainless steel. Alternatively, the metallic layer can be made of other materials such as gold, brass, or other suitable conductive materials that yield relatively good chemical inertness and low absorptive and adsorptive qualities. The liner 302 can also include a co-polymer adhesive (such as a thermo-set adhesive) 307 that is used to adhere the liner to the outer jacket 304 (FIG. 3A) during the extrusion process.

One advantage of using the liner 302 shown in FIG. 3B is that the tube can be lined using a relatively simple manufacturing process, which can be similar to the process to create the assembly of FIG. 2, in which the metallic liner is formed into a tube over a forming die and a suitable plastic material such as polyethylene or PVC is extruded over it. In cases where the composite tubing described in this invention is intended for use in environments requiring a stringent smoke and flame rating, such as plenum and riser environments described by the National Electrical Code, it is undesirable to use polyethylene in the outer jacket (204 & 304) due to the exorbitant smoke that is generated by most kinds of polyethylene materials when they burn. As an alternative, one of any number of flame retardant PVC materials may be used for this purpose and in doing so, the assembly can be certified under the most stringent of tests, such as NFPA 262 or UL910, which is used to qualify cables for use in plenum environments. Using PVCs also results in a tubing arrangement that is less stiff or more flexible, which is a desirable property as this makes such tubing easier to install in a building environment, particularly as it is incorporated to form a structured cable such as that depicted in FIG. 6.

One consideration in using a softer more flexible material such as PVC over polyethylene is that it provides less retention capabilities to protect the inner liner 202 (FIG. 2) or 302 (FIG. 3A, 3B) from permanently deforming should the assembly be subject to crushing or excessive bending. One factor which results in permanent deformation of the inner liner when subject to these conditions is the thickness of the liner's metallic layer. Thus, when constructing the outer jacket of PVC, it is desirable to make the metal layer as thin as possible, and this makes the composite liner 302 of FIG. 3B highly suitable, as this metallized layer can be made very thin, using vapor deposition or similar techniques. For example a common maximum deposition thickness from vapor deposition techniques is 2000 Å, which is approximately 250 times thinner than available stainless steel foil, such as that which might be used for liner 202. As a result, a composite tube utilizing the composite liner depicted in FIG. 3B will be highly flexible and crush resistant. Additionally, a deposition thickness of 5000 Å or more is possible using more various techniques. Having a surface coating with a thickness of this magnitude may be desirable to promote better conductivity and abrasion resistance. Conversely, depending on the sputtering process used, a deposition thickness of 200 Å or less may be sufficient to provide sufficient performance against adsorption and absorption of constituents within air samples, while also providing an acceptable level of conductivity to promote good particle transport efficiency.

For example, where the liner 302 of FIG. 3B is utilized, the substrate 306 is made of 0.001 inch thick Mylar® and 1000 Å of stainless steel is deposited on its surface. Mylar is a preferred material for the substrate 306 because it is strong and tear resistant, which is advantageous for the extrusion process, in which the substrate is subject to large forces as it is pulled through the extrusion head. In addition, in this configuration, due to the very good performance of the thin metallized surface 305 to spring back to its original shape, the tubing can be made with a relatively large inner diameter (ID) while still being highly crush resistant and resistant to kinking and other sources of permanent deformation. For example, in an exemplary embodiment where the outer diameter (OD) is ⅜ of an inch using the inner lining of FIG. 3B, the tube can be constructed with an ID of 0.310 inches. Such a large ID is desirable as it results in less restriction to airflow, compared to that of a smaller ID, as air samples are drawn by the system, thus reducing pressure drop in a system for a given flow rate. This helps to reduce pump capacity issues as well as to promote better particle transport efficiency on air samples taken by the system. The reason for the latter is that air sampling systems, such as that described in U.S. Pat. No. 6,125,710 tend to operate at relatively high flow rates (typically 20 liters per minute or more). At these flow rates, several psi of pressure drop can be realized in a system, due primarily to frictional losses along the length of the tube. Pressure drops of this magnitude have a large impact on the density of the flowing gas (air), resulting in variations in the velocity of the gas as it travels along the length of the tube. This change in velocity or acceleration has a tendency to cause particles to drop out of the flow stream, and are therefore lost from the sample, as a result of the inertial affects due to particle mass.

Figure 4:
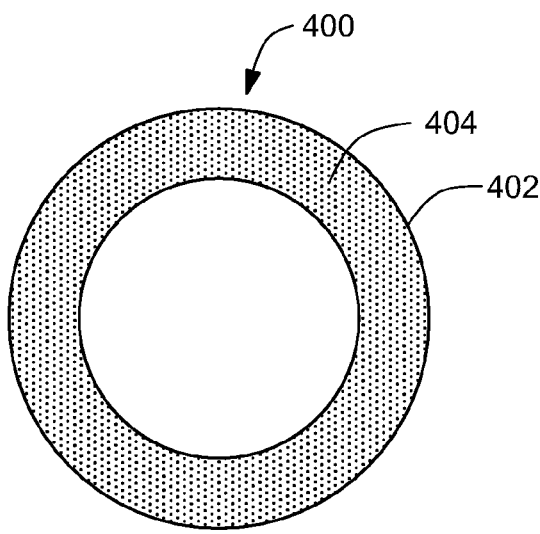
FIG. 4 is a schematic representation of another embodiment of a composite tubing in accordance with the present invention.

FIG. 4 shows an exemplary composite tubing 400 in which a suitable host material 402 is impregnated with a metallic material 404. The tubing 400 can be provided in various embodiments having uniform and non-uniform distribution of metallic material along the cross section of the tubing.

In one particular embodiment, the tubing 400 includes finely divided stainless steel flakes with polyethylene, mixed immediately before the extrusion process. The quantity of stainless steel should be sufficient to provide occlusion of the inner surface of the tube to any significant amount of polyethylene on the exposed surface. The stainless steel flakes can range in size from several tens of microns down to a fraction of a micron in size. This variation has the working properties of polyethylene tubing with nearly the same chemical inertness as stainless steel tubing while also providing an electrically conductive inner surface that inhibits electrical charge from collecting on the inner surface as air samples are drawn to promote efficient particle transport.

In another embodiment, the host material 402 is Teflon® and the metallic material 404 is finely divided stainless steel. This combination can yield an inner surface that has lower absorption and out-gassing properties than stainless steel impregnated polyethylene. Teflon®) has inherently low absorption and out-gassing properties allowing the formation of tubing using a process that is less dependent on the ability to control the packing density of the metallic material. Variations in the packing density of the metallic material can cause the inner surface area of the tubing to take the undesirable properties of the polyethylene where the packing density is relatively low.

FIGS. 5A and 5B show another exemplary embodiment of a composite tubing 500 in accordance with the present invention having an inner surface 502 formed in part from a nonmetallic material 504 and in part from a metallic material 506. The tubing 500 includes metallic strips 506 imbedded in the surface of the nonmetallic material 504.

In one particular embodiment, the metallic material 506 that forms the inner surface of the tubing 500 is substantially flush with the surface of the nonmetallic material 504. The metallic material 506 provides a conductive path to dissipate electrical charge that is transported as a result of airflow through the tubing to promote efficient transport of particulate matter through the tubing for air sampling purposes.

Gaps 508 between the conductive metallic material 506 should be sufficiently small so as to ensure that only a negligible electric field can be established between conductors as a result of the air flow rate that is applied through the tubing for a given sampling application. In one embodiment, the metallic material 506 includes stainless steel and the nonmetallic material 504 includes Teflon®.

FIG. 6A is a cross-sectional view of an exemplary embodiment of a structured assembly 600 including a composite tubing 650 and various groups of conductors that can be used within an air sampling system in which the assembly may be installed. FIG. 6B is an isometric view of the structured assembly 600 of FIG. 6A. The groups of conductors, which can be helically wound around the tubing 650, can provide power, communications, and various signals that may be monitored within a system. The structured assembly 600 simplifies and lowers the cost of the installation of the power and communications cables (as well as the tubing) provided with such systems.

The exemplary structured assembly 600 is well suited for use in an air sampling system, such as the illustrative air sampling system 700 of FIG. 7. The system 700 can be installed in a building and can form a part of a building control system having controllers distributed throughout a building communicating over one common network. The system 700 can include a sensor suite and controller 702, which can be remotely located, coupled to one or more node controller modules 704*a,b*. Termination points 706 can be located in various rooms to take air samples that are passed to the sensor suite 702 via the node controller 704*a*. The node controllers 704*a,b* can be networked together and controlled over a network by the central controller 702. Each node controller 704 controls a valve that is dedicated to each room from which an air sample is to be taken. The termination points 706, node controller 704, and sensor suite 702 can be connected via the structured assembly 600 of FIG. 6, for example.

Air samples are taken from each room in the system in a multiplexed fashion and brought back to the sensor suite 702. In addition, discrete sensors (such as for temperature and relative humidity) may be disposed within the termination point locations shown for each room and the data associated with each may be sampled by each node controller, either by way of a serial connection to each termination point or by connecting analog and/or digital signals between the termination point and the node controller. Further details of an exemplary air sampling system are discussed in U.S. Pat. No. 6,125,710.

Referring again to FIG. 6, the assembly 600 includes a composite tubing 650 having a metallic layer 652 and a tubing jacket 654. In a region 602 between a cable jacket 604 and the tubing jacket 654, various cables and wires are disposed. In an exemplary embodiment, the assembly 600 includes first, second, third, and fourth cable structures 606, 607, 608, and 609. Cable structures 606, 607, and 608 are used to provide a combination of power, signal and communication connections for the system.

The fourth cable structure 609 is used to provide a dedicated sensing function, which helps to optimize the performance of the system 700. Additionally, the assembly 600 includes a ripcord 610 to aid with the removal of the outer jacket 604 during field installation of the cable. Ripcords are a common feature to structured cable assemblies. For example, many of the cables in the composite cable line (for example, Belden 7876A composite data, audio, video, security, and control cable) offered by Belden CDT Inc., a major wire and cable manufacturer, include ripcords.

In one particular embodiment, the first cable structure 606 includes a 22 AWG twisted pair to carry signals and the third cable structure 608 includes a 22 AWG-TSP having a drain wire 608*a* and foil shield 608*b* to provide communications for some connections and signals for others. The second cable structure 607 includes an 18 AWG triad-type stranded cable to carry power for the system components.

The function served by cable structures 606, 607, and 608 varies depending on which portion of system 700 (FIG. 7) the cable 600 is used in. For example, when making connections between node controllers 704*a,b* or 702, (FIG. 7) the second cable structure 607 will typically be used to provide power from a power supply (residing within or in proximity to the Sensor Suite 702) to the various Node Controllers in the system. For the system 700 this will typically be 24VAC power and ground, however, different embodiments of this system can be made to operate off of other power sources (for example +/−15 VDC and ground) that would likewise be supplied through cable structure 607. When connecting between node controllers 704, or a node controller 704 and the Sensor Suite 702 the third cable structure 608 serves as the network cable over which the node controllers 704 and the sensor suite and central controller 702 communicate. For these connections, in an exemplary embodiment of system 700 the third cable structure 608 forms the backbone of a data communications network having an EIA485 (or equivalent) physical layer. It should be obvious to those skilled in the art of data network design that networks of this type often utilize a twisted-shielded pair of conductors with a drain wire, as has been specified for the third cable structure 608, in order to both constrain the characteristic impedance of the cable and to provide a degree of noise immunity to the network. Further, when the structured cable 600 is used to make connections between node controllers 704 or between node controller 704*a* and the sensor suite 702, the first cable structure 606 will typically not be utilized, or will serve some ancillary and non-predetermined purpose that may arise in custom applications of system 700.

When making connections between a node controller 704 and a termination point 706, the second cable structure 607 will typically be used to provide power and signal ground to the discreet sensor devices and instrumentation that resides at the termination point 706. Additionally, when connecting to termination point 706, the first and second cable structures 606, 608 may be used to connect the signal outputs from the various sensors located within 706 to the node controller 704 which samples these signals and communicates them back to central controller 702. Examples of the sensor types that may exist at 706 include temperature, relative humidity, and ozone sensors.

The fourth cable structure 609 provides sense lines to optimize the timing sequence for air samples. In one particular embodiment, the sense lines are provided as 26 AWG twisted pair wires. The sense lines 609 are used to measure the distance between the sensor suite 702 of FIG. 7 and each termination point 706 within the system, in order to estimate the transport time of each air sample from each location to the sensor suite. The flow rate, and therefore transport velocity will usually be regulated at the sensor suite 702. Therefore the sample transport time for each of the sensed locations may be computed by dividing the estimated distance by the same velocity. This is helpful in optimizing the sampling rate of the system, because in larger systems the transport distance may be a few hundred feet, resulting in appreciable transport times. For example, at a flow velocity of twenty feet per second, a sample taken over four hundred feet has a transport time of twenty seconds.

In addition to estimating transport time, measuring transport distance can be advantageous when the sensor suite 702 is used to perform particle measurements. Even though the transport efficiency of particulates is good through the inventive tubing, particle loss for larger particles (e.g., greater then 1 uM) may vary significantly with transport distance, especially when samples are taken over a distance of several hundred feet of tubing. However, the percentage loss is fairly predictable with distance at a given flow rate and thus, knowledge of the transport distance provides a way to compensate for this loss.

Figure 7:
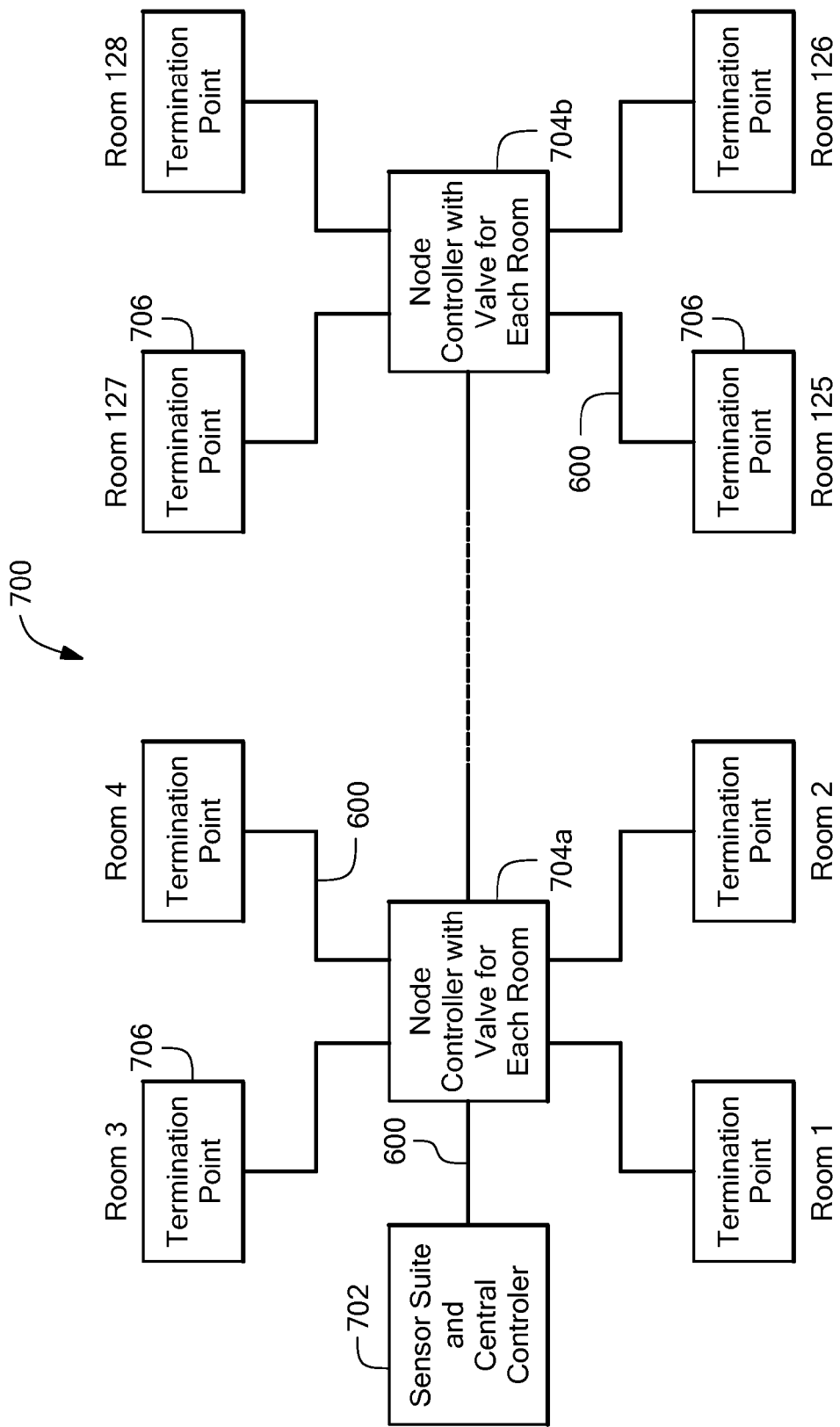
FIG. 7 is a block diagram of an air sampling system having composite tubing in accordance with the present invention.
Figure 8:
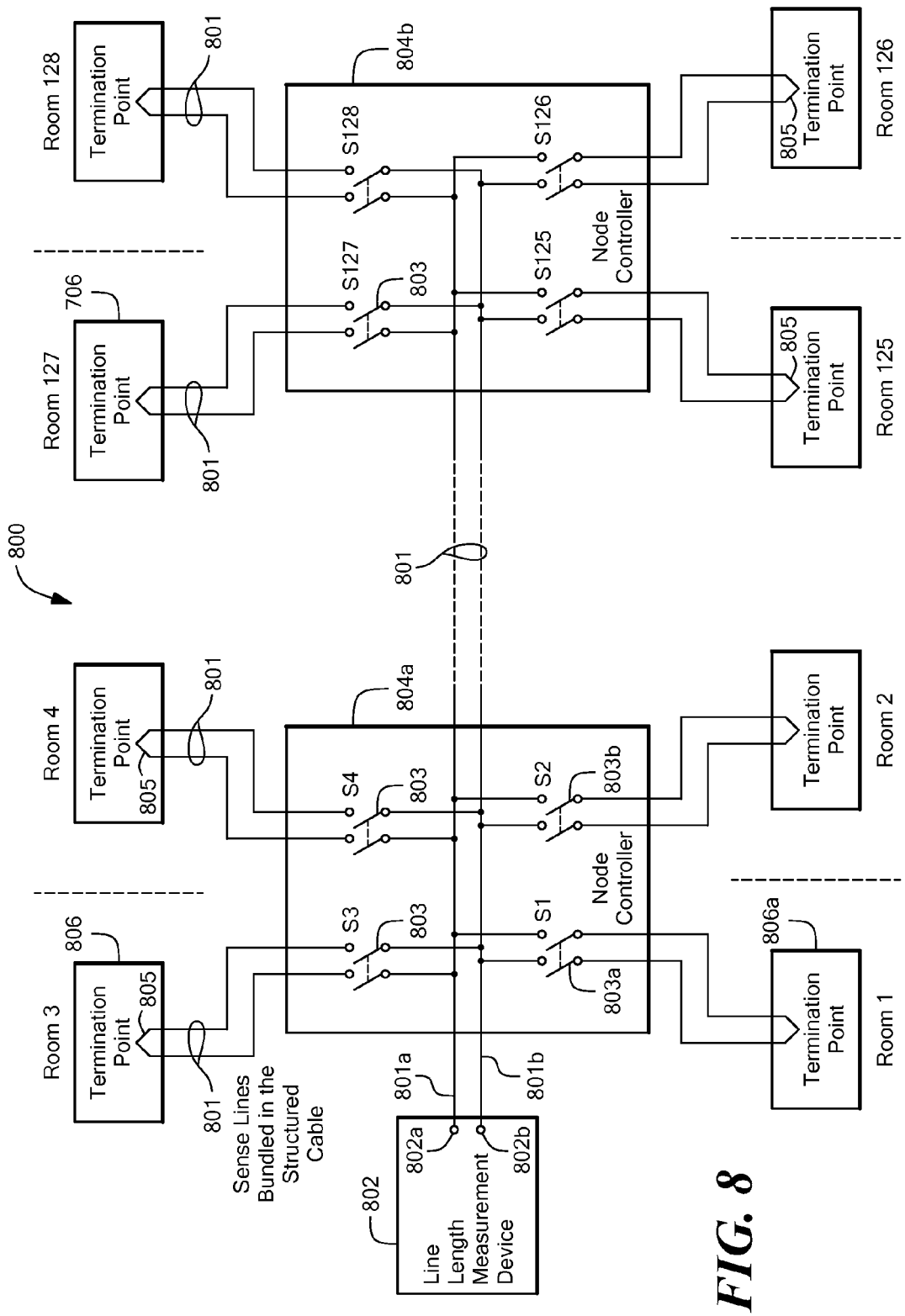
FIG. 8 is a schematic that illustrates an embodiment of a subsystem that can be applied to the system of FIG. 7 to optimize its performance.

FIG. 8 is a schematic view 800 of the electrical circuits created by the sense lines 801 as they are distributed by way of a structured cable 600 throughout the system 700 depicted by FIG. 7. Termination points 806 therefore correspond with 706 in system 700 and node controllers 804 correlate with node controllers 704. The line length measurement device 802 is typically housed within the sensor suite and central controller 702 or in close proximity (typically within 40 feet) to 702. As shown in FIG. 8, and as has been illustrated in FIG. 6, the sense lines are preferably a pair of wire conductors 801a,b. This conductor pair is distributed through system 700/800 where it is connected to the various node controllers 804, termination points 806, and to a line length measuring device 802. Each of the node controllers 804 contain a number of pairs of electrical switches 803, which are used to selectively complete a circuit between the line length measurement device 802 and the individual termination points 806 in order to measure the distance between the termination point 806 and the line length measurement device 802. Techniques for making the distance measurement are dependant on physical properties of the conductor pair 801a,b that vary with conductor length. For example, in one embodiment the distance measurement is based upon the measurement of the total ohmic resistance of the conductor pair 801a,b between the line length measurement device and a given termination point 806, as measured between 802a and 802b. It should be obvious to those skilled in the art of electronics that there are a great variety of circuits that can be designed to make such a measurement. For example, in one embodiment a current source may be applied as an electronic circuit component within line length measuring device 802 to generate a precise electrical current that can be made to flow out of point 802a, through the sense line 801a down to the spliced connection 805 and back through 802b. Spliced connection 805 could be made by twisting the ends of the conductor pairs 801a,b together at termination point 806, or connecting 801a,b together using a twist-on wire connector, or any other suitable means used to join two electrical conductors together. The resultant voltage between points 802a and 802b is simultaneously measured by a separate circuit within 802, which signal is proportional to the resistance between 802a and 802b, which is proportional to the distance to the termination point. When using a method such as this, sense lines 801a,b are connected together to form a splice connection 805 at each termination point 806 and the total resistance of the circuit (formed by the conductors in 801a and 801b, the closed switch 803, and spliced connection 805) is measured by the measurement device 802.

As a further example, using this resistance measurement method, in order to measure the distance between termination point 806a and the line length measurement device 802, the switch pair 803a in node controller 804a would be closed while keeping all other switches 803 in the system 800 open and the resistance of the resultant circuit between 802a and 802b is measured. Note that the actual length of the circuit is twice the actual distance being measured because of the combined lengths of both conductors 802a and 802b. This helps to enhance the resolution of such a measurement system while minimizing the magnitude of the current that must be sourced from line measurement device 802.

In an exemplary embodiment, the sense lines 801 are a 26 AWG solid twisted pair of copper wire that can be, for example Beldon Equivalent 9976, which has a resistance specification of 40.81 ohms per thousand feet. Alternatively, wire of finer or coarser gage and using different configurations, such as stranded wire, and made of different materials, such as aluminum or other materials may be used. However, the material of choice should have a relatively low temperature coefficient of resistivity to ensure the accuracy of the measurement is relatively insensitive to temperature because temperature may vary dramatically throughout a given building through which cable assembly 600 is installed.

Resistance varies with temperature according to Equation 1 below:

$$R_T = R_{20}[1+\alpha(T-20)] \quad \text{(Eq. 1)}$$

where,
$R_T$=Resistance in ohms at actual temperature
$R_{20}$=Resistance in ohms at 20° C.
α=temperature coefficient of resistivity
T=Actual temperature in ° C.

In a typical commercial building environment, including common areas, rooms, interstitial spaces, and penthouses the typical operating temperature range the cable assembly 600 will be exposed to is 0 to 40° C. As was previously stated, in the preferred embodiment of this invention, the sense lines 801 will be made of copper. For copper, α=0.00393° $C.^{-1}$ which, based on Eq. 1 means the tolerance due to temperature on distance measurements based on resistance with copper is approximately +/−8%, assuming a standard temperature of 20° C. and an operating temperature range of 0 to 40° C. This level of accuracy is sufficient for most systems 800 where the transport distance is 500 feet or less.

In another embodiment line length measurement device 802 may incorporate a time domain reflectometer (TDR) to measure the distance between a termination point 806 and device 802. Such an approach is based upon applying a high bandwidth electrical pulse in either a differential or single-ended manner to lines 801a and 801b and measuring the elapsed time it takes for the pulse(s) to propagate down the line 801 through the selected switch 803 to the termination point 806 and back again. Using a TDR to measure the length of a cable is a well-established practice.

It should be noted that to ensure that the distance measurement performed using the sense lines is reasonably representative of the actual tube length, the ratio of the length of these conductors to that of the tube should be controlled. This is one feature of the structured cable assembly, as it aids the performance of the air transport tubing.

The exemplary embodiments disclosed herein having metal-lined tubing provide enhanced particle transport efficiency performance compared to known tubing made with materials that are highly non-conductive. This is due to the conductive properties of the metallized liner, which tends to minimize deposition due to electrostatic effects, as discussed. However, another source of particle loss, a mechanism known as thermophoresis, can also have a noticeable impact on transport efficiency. Thermophoresis refers to the migration of particles as a result of forces due to a temperature gradient, where the net force on a particle is in the direction of the region of lower temperature. This can be a factor affecting particle transport where the structured assembly 600 is installed in a building where large temperature gradients exist between the termination point 706 and various areas within the building over which the assembly 600 is routed. For example, the cable assembly 600 may be routed through a penthouse or interstitial space that may at times (during winter months, for example) be at a temperature that is substantially lower than that of the room (termination point 706) from which air samples are drawn. For example, it is known that the deposition rate of 0.5 um particles on a surface could be reduced by ten fold by maintaining a temperature difference of 10° C. between a deposition surface and the air that the particles are suspended in. Thermophoretic forces tend to be inversely related to particle diameter and will be most pronounced with particles that are 1 um in size and smaller.

In another aspect of the invention, a structured assembly 600 compensates for thermophoretic forces, as well as providing some degree of countermeasure for other deposition forces, such as gravitational effects and coulombic forces (electrostatic effects) affecting particle transport. This may be accomplished by disposing a heat source along the length of the composite tubing 650 that is sufficient to maintain the average temperature of the inner liner 652 above the temperature of the air sample that regularly passes through the tube 650.

Additionally, another reason for heating the tubing is to prevent condensation of certain VOC's or other gases, including water, that could condense out of the air while they are being transported to the sensor suite through the tubing.

In one particular embodiment shown in FIG. 9 the assembly 600 of FIG. 6 is modified to form the assembly 900 by adding one or more heater elements 901 to the structured cable assembly. Heater element 901 may be one or more resistive heating elements, made of materials such as nichrome, tungsten, nickel, stainless steel, or other material suitable for rendering a heater function through which an electrical current can flow, resulting in power dissipation and a temperature rise along the length of the conductor. This conductor may have a cross section that is either circular or flat so that the conductor is ribbon shaped.

In the illustrated embodiment, the heater element 901 is made of 28 AWG tungsten wire. The source of this electrical current is contained as a separate electronic module that is part of the sensor suite 702 (FIG. 7), from which the average temperature of heater element 901 may be controlled by either applying a predetermined electrical current to the medium based on the total length of cable 900 or if the material's temperature coefficient is relatively large, such as that with tungsten or nickel, as an alternate embodiment, the temperature of the heater element 901 may be precisely controlled using well established methods for controlling the temperature of a temperature-dependant resistive material such as, for example, techniques that have been developed for controlling the temperature of a hot wire anemometer. See, for example, U.S. Pat. No. 4,523,461.

In one particular embodiment, however, where tungsten is used, a constant current is applied to the medium. Generally, a heater element would most typically be utilized within assembly 600/900 as it connects between Node Controllers 704 (for example between 704*a* and 704*b*) shown in FIG. 7, as these connections typically involve the longest lengths of assembly 600 as it is routed through the structure of a building, sometimes over a distance of several hundred feet. However, there are many cases where a heater element could advantageously be applied within assembly 600/900 as well as between Node Controllers 704 and their respective termination points 706, as large temperature gradients can often be realized between these connection points within a building and this can significantly contribute to particle loss.

Another factor that influences particle transport through a tube, is the ability of the inner surface of the tubing medium to establish an electrical charge. As an electrical charge becomes established upon a surface, particulate matter that is suspended above that surface will have a tendency to be attracted to the surface if the charge on the surface and the charge on the particle are opposite in polarity. One of the advantages of the conductive liner 652 described herein is its ability to disperse charge, therefore resulting in a relatively low charge per unit area compared to that of a poorly conductive surface. In some cases, however, it may be advantageous to provide an added conductive path through which charge may flow from the conductive liner 652 to some other electrically conductive medium to substantially reduce the amount by which a charge can develop over the surface of conductive liner 652. As an example, the conductive liner may be electrically connected to an electrical ground within a building, or it may be connected to the frame of a building, or some other component of a building that either offers a low impedance path to ground or another medium through which the charge can be dispersed over. The conductive path for charge to flow from liner 652 may be established using any number of techniques involving providing either a single connection to ground or multiple connections to ground throughout a system.

FIG. 10A is a schematic view 1000 of the distribution of tubing 650 distributed by way of structured cable 600 throughout the system 700 depicted by FIG. 7. The tubing 650 (also labeled as 1001 in FIG. 10A) is distributed through system 700/1000 where it is connected to various valves 1003 contained within node controllers 1004, and it is connected between valves 1003 and termination points 1006. Also shown is an optional grounding connection 1010, which may be utilized to electrically connect the inner liner 652 to a ground within the building in which system 1000 is installed, thus providing a path for charge to flow out of system 1000.

In one embodiment, the conductive inner liner 652 of the various sections of tubing 650 shown in system 700/1000 are electrically connected together so that any amount of charge that is applied to any of the tubing section 1001*a,b,c,d,e,f,g,h,i* is equally dispersed throughout tubing section 1001*a,b,c,d,e,f,g,h,i*. These electrical connections may, for example, be made by using electrically conductive barbed fittings at valves 1003 and provide a means to electrically connect a fitting on one side of the valve 1003 to a fitting on the other side of the valve 1003.

FIG. 10B depicts the way tubing is joined to a valve 1003 within a node controller 1004 using this method, involving barbed fittings 1007*a,b* connecting to each side of valve 1003. Barbed fittings, which are well known to those experienced with pneumatic systems, are commonly used with most types of flexible tubing and are used to make connections by pushing the tubing over the barb section of the fitting. (General examples of a barbed fittings include those of the Thermobarb® product line by NewAge Industries, Inc.) By making such a connection with tubing 1001, each fitting is in contact with the conductive inner liner 652 of the tube 1001. For the purposes of this invention, the fitting 1007 may be made of or coated with any type of conductive material including: metals (such as, for example, brass, bronze, iron, steel, stainless steel, and aluminum), conductive plastics, conductive composite materials, or conductive paint. Further, in one embodiment, valve 1003 may itself be made of a conductive material such as, for example, stainless steel or some other metal and thus, when connected to fittings 1007 and tubing 1001 as shown provides an electrically continuous path for charge to flow between tubing sections 1001a and 1001b.

Figure 10A:
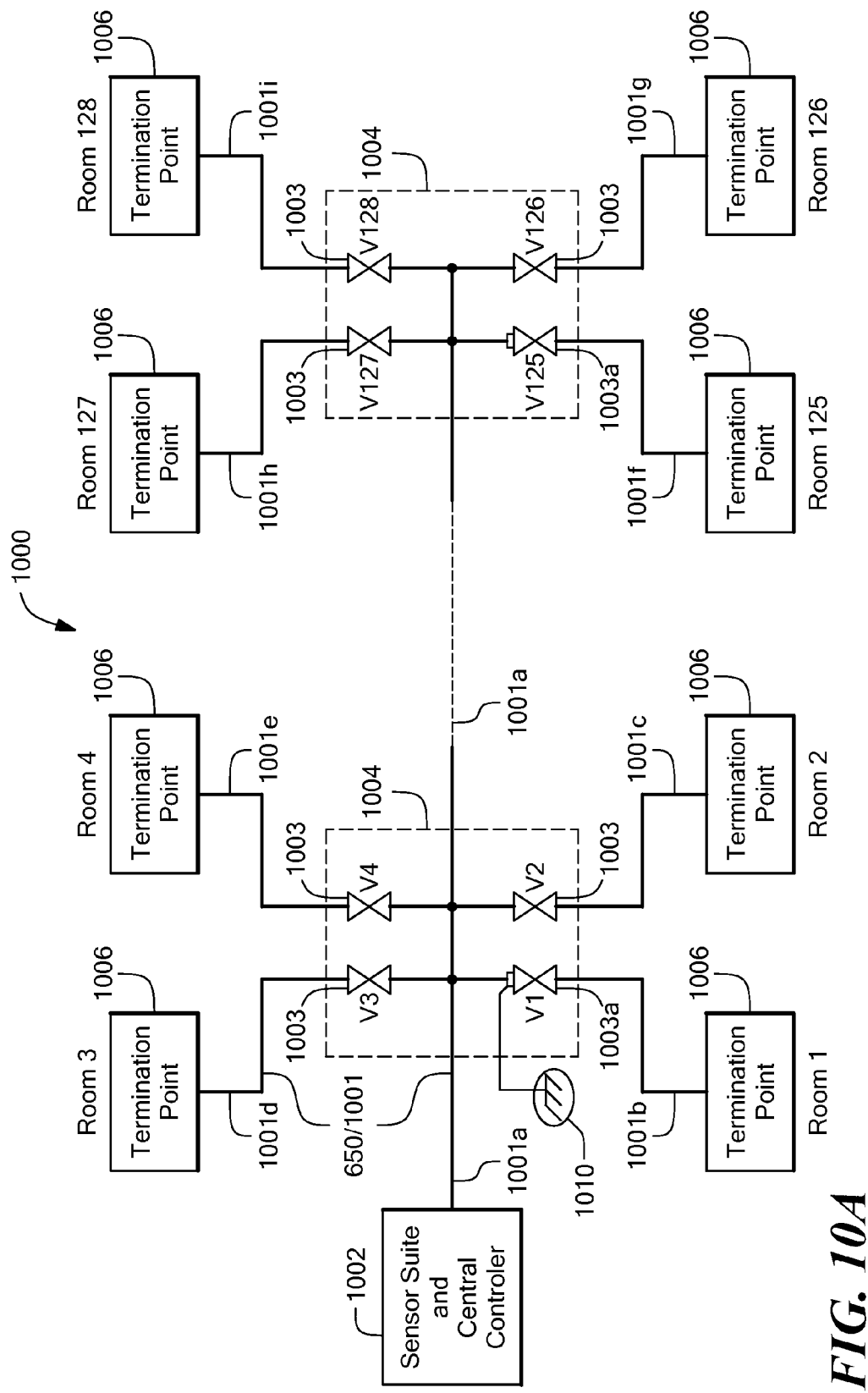
FIG. 10A is a schematic depiction of the tubing in an air monitoring system.
Figure 10B:
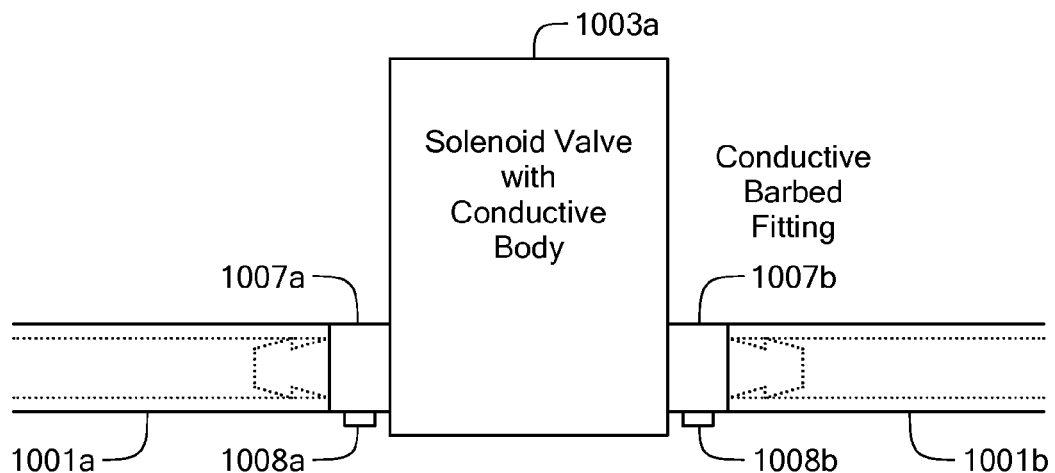
FIG. 10B is a schematic depiction of a tubing joined to a valve within a node controller.
Figure 10C:
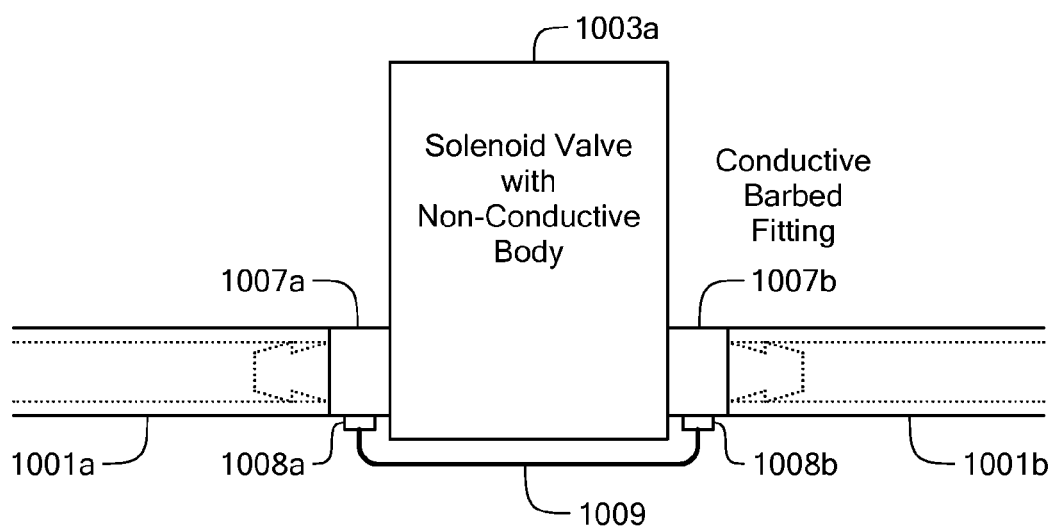
FIG. 10C is a schematic depiction of a tubing joined to a valve that includes a shorting strap within a node controller.

In an alternate embodiment, as shown in FIG. 10C, if valve 1003 is made of a nonconductive material a shorting strap 1009, connected to terminals 1008a of fitting 1007a and 1008b of fitting 1007b, may be provided to electrically connect the inner liners 652 of tubing 1001a,b together. Such a conductive strap 1009 may be a copper wire, or a wire made of some other conductive material that is suitable for this purpose. The terminals 1008a,b may be screw-down type clamps capable of fastening a wire, such as strap 1009 to fitting 1007, and it may also be used to secure the optional ground connection 1010. Additionally, optional ground 1010 may be provided at one or multiple locations throughout system 1000.

In a further embodiment, instead of using barbed fittings 1008, a conductive path is provided for transferring charge from conductive inner liner 652 through the jacket 654 of tubing 650 by constructing the jacket 654 using a material that is conductive. For example, jacket 654 could be made from a composite of plastic that has been impregnated with finely divided metal flakes, such as that used in tubing 400. Jacket 654 can also be made from a plastic resin that has been embedded with carbon powder or fiber or any number of other conductive filler compositions.

Figure 11:
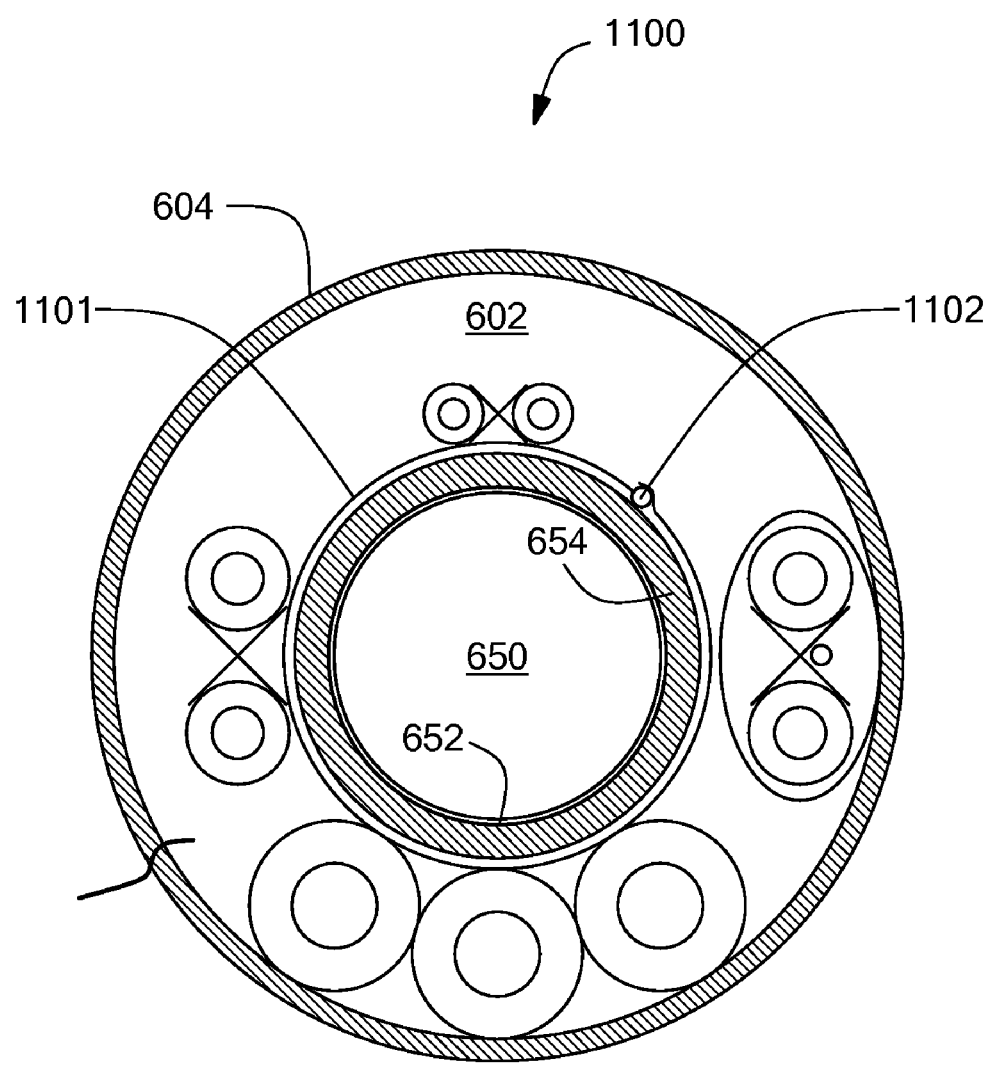
FIG. 11 is a cross-sectional view of a tubing that can be used in an air monitoring system.

FIG. 11 depicts an exemplary embodiment where the tubing 650 is additionally wrapped with a conductive shield 1101 and a conductive drain wire 1102 is disposed between conductive shield 1101 and the conductive tubing jacket 654 to form a low impedance connection between these three elements (654, 1101, and 1102). Conductive shield 1101 may be composed of metallic foil, such as aluminum foil, an aluminum-polyester-aluminum laminate (such as that which is common to most commercially available shielded cables), or any other suitable conductive material. Likewise, drain wire 1102 may be a conductive wire such as the copper drain wire typically found in shielded cables. However, the drain wire 1102 may be composed of other suitable conductive materials as well.

The drain wire 1102 may be connected to ground connection 1010 of system 1000 in order to provide a conductive path for charge to flow from conductive inner liner 652 to tubing jacket 654, to the conductive outer material or shield 1101, and then ultimately through drain wire 1102 to ground. When applying cable assembly 1100 to system 1000 tubing and making only one ground connection the conductive inner liner 652 between sections 1001a,b,c,d,e,f,g,h,i may be electrically connected together by splicing drain wires 1102 from each section 1001a,b,c,d,e,f,g,h,i together. As is the case for the embodiment with barded fittings, the embodiment using cable assembly 1100 may also be grounded at multiple locations throughout system 1000. When doing so, it is generally not necessary to splice the drain wires 1102 from each section 1001a,b,c,d,e,f,g,h,i together.

The interconnection of the conductive inner liner 652 from tubing sections 1001a,b,c,d,e,f,g,h,i as well as providing an added electrical path such as ground connection 1010 for charge to flow, are passive methods to limit charge buildup within a system. Alternatively, however, active methods may be used to either control the electrostatic charge buildup on inner liner 652 or to control the way in which particles interact with the electrostatic charge on surface 652 in order to aid in transporting particles as air samples are taken from various termination points 1006 throughout system 1000.

In one embodiment, air samples that are drawn through tubing 650 in system 1000 may be exposed to an ionizing source that either positively or negatively charges particulate matter drawn from each air sample taken from termination points 1006. In this embodiment, a voltage is applied to the conductive inner liner 652 of tubing 650 in order to repel the charged particulate matter from the surface of the conductive liner 652, thus improving the transport efficiency of particulate matter through system 1000. Exemplary ionization sources for ionizable fluid media are described, for example, in U.S. Pat. Nos. 6,693,788, 4,689,715, 3,711,743, and 3,613,993, all of which are incorporated herein by reference. More generally, however, ionization devices can utilize any number of electrodes that are exposed to the ionizable fluid media (such as air) and are coupled to a high voltage source (typically 5K volts or more).

Figure 12:
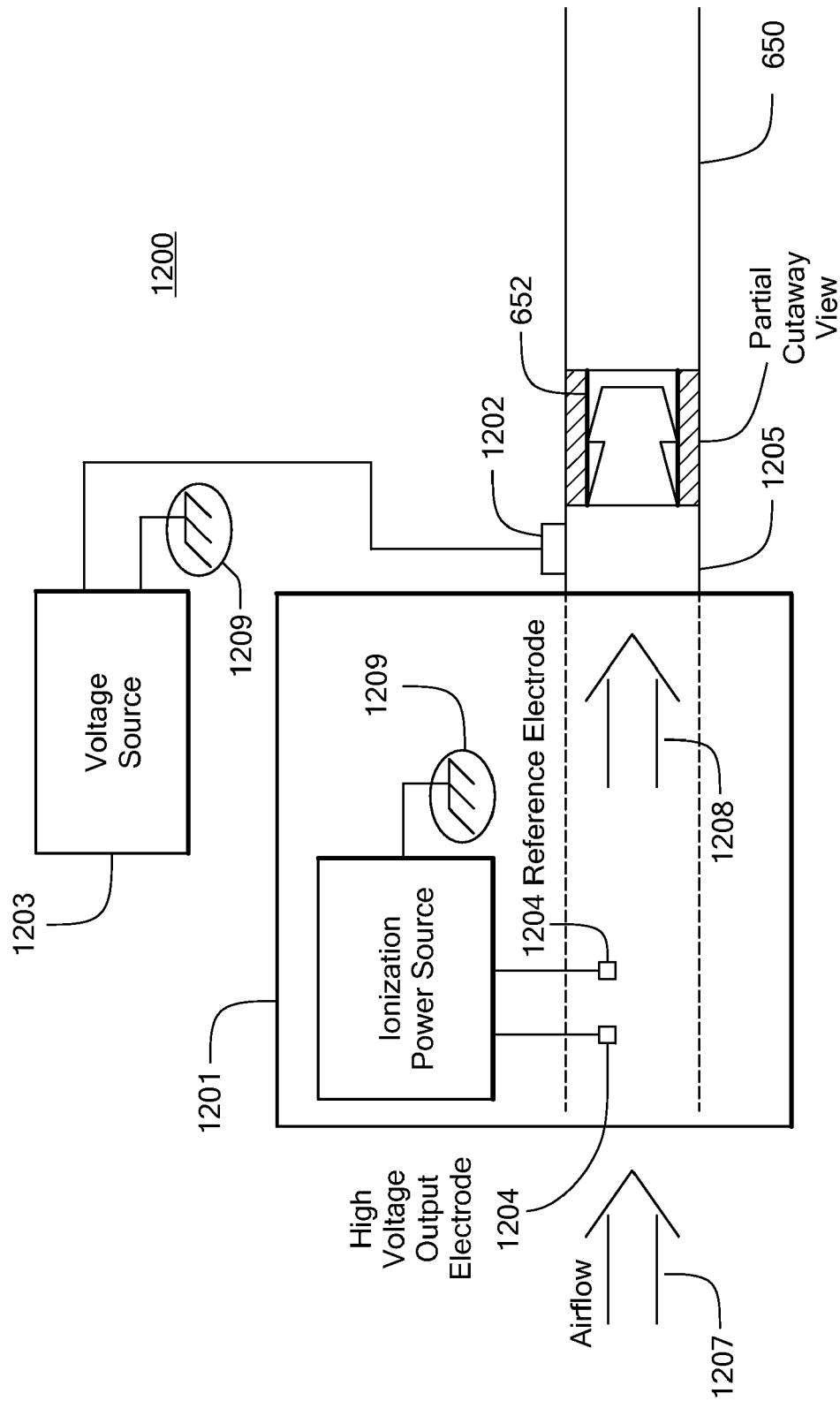
FIG. 12 is a schematic depiction showing an ionization source applied to an airflow stream in conjunction with tubing.

FIG. 12 illustrates an exemplary embodiment 1200 of the application of an ionization source 1201 applied to the airflow stream in conjunction with tubing 650. In this embodiment, a conductive barbed fitting 1205 is being used to provide an electrical connection to the conductive inner liner 652 to which a voltage potential may be applied by electrically connecting the output of voltage source 1203 to barbed fitting 1205 using screw-down clamp 1202. However, other suitable ways of connecting to conductive inner liner 652 may also be used. Here, voltage source 1203, which is connected to the same reference 1209 as the ionizing power source, may either be a DC voltage or a time varying voltage having a DC component. The magnitude of this voltage may be any value ranging from several volts to several thousand volts. Voltage source 1203 can be considered to be an active device. Because of the potential hazard that may be created as a result of the potentially large voltage that may be applied to conductive inner liner 652, voltage source 1203 can be designed with energy limiting features by substantially limiting its current sourcing capabilities. Air flow stream 1207 flowing into ionization source 1201 becomes ionized by electrodes 1204 which have a large voltage potential applied between them from ionization power source 1206. The resulting ionized flow stream 1208 flows into tubing 650 through barbed fitting 1205 and, due to charge established via voltage source 1203 on conductive inner liner 652, the ionized particles within flow stream 1208 will have a tendency to be repelled from the surface of conductive inner liner 652, resulting in an enhancement to particle transport throughout tubing 650. For purposes of this invention an ionization source 1201 may be applied at numerous locations throughout system 1000.

While the inventive composite tubing is well suited for use in system 700, as described, it is also well suited for use in other types of air monitoring systems designed to transport air samples and make remote measurements of various characteristics of the air with any number of sensors. For example, the tubing is well suited for use in multi-point air sampling systems such as that described by U.S. Pat. No. 6,241,950, which is incorporated herein by reference. Other types of similar systems, which may also benefit from the inventive tubing, include systems used to provide monitoring functions for the detection of refrigerant leaks, and other toxic gas monitoring applications. These are commercially available systems that are often used to monitor the presence of a refrigerant leak in gaseous form at one or multiple locations within a building (especially in the vicinity of chilled water plants, air handlers, and other refrigeration systems) using one or a number of shared sensors. Such systems may also be used to monitor carbon dioxide (CO), oxides of nitrogen ($NO_X$), and other toxic gases and building pollutants, or pollutants within other confined spaces such as parking garages.

Figure 13:
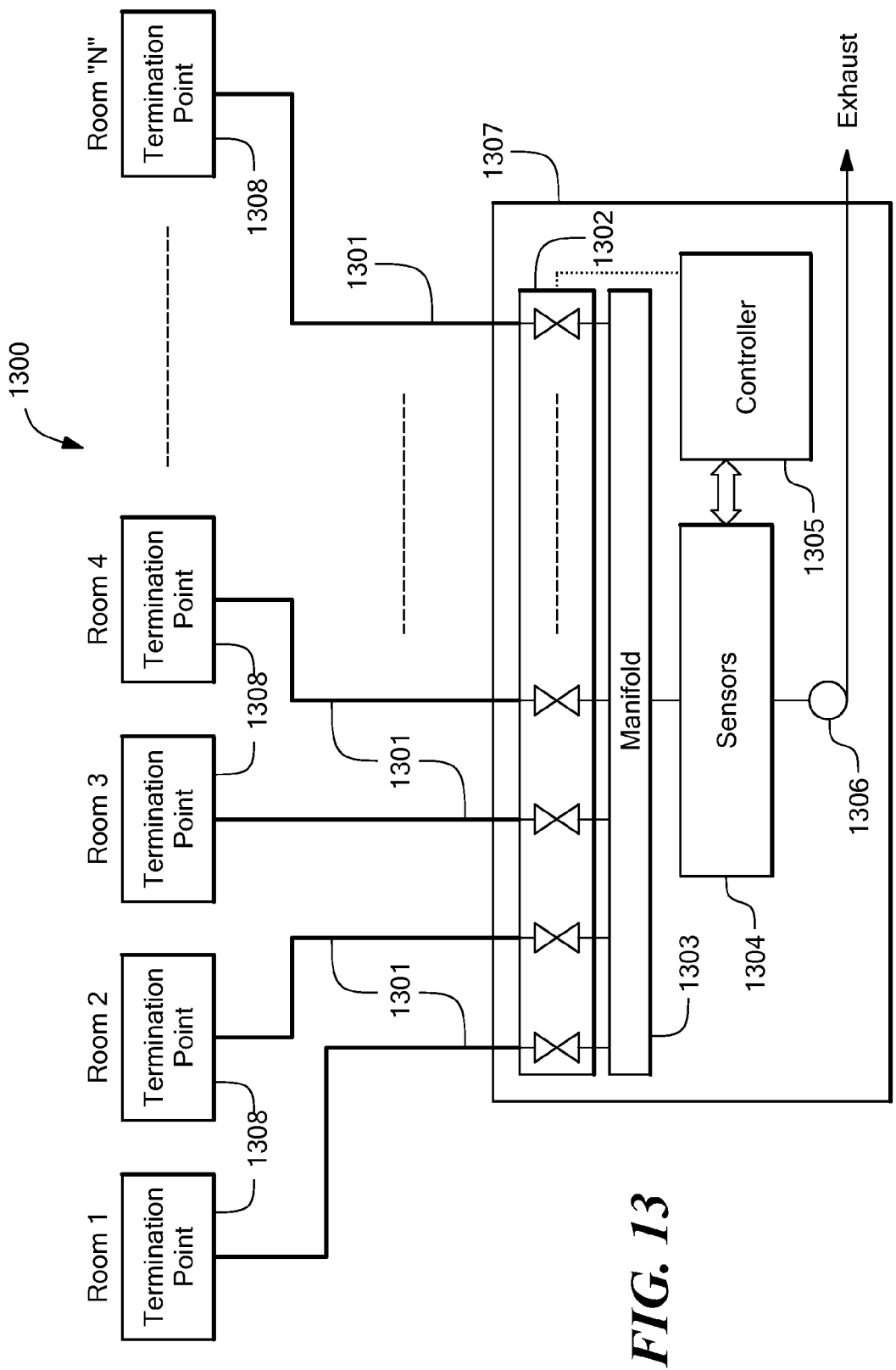
FIG. 13 is a schematic depiction of a multi-point air sampling system.

In systems such as that described by U.S. Pat. No. 6,241,950, for example which is incorporated herein by reference, as well as the aforementioned systems used to monitor refrigerants and other (toxic) gases, both the sensor for making air parameter measurements and the air intake valves for switching samples from locations monitored by the system are placed in a common location within the building, and they are typically placed within a common enclosure. FIG. 13 is a generalized view of such a system, which has a plurality of input ports connected via tubes 1301 to each room termination point 1308 of interest. The termination point 1308 may simply be the location that the end of each segment of tubing 1301 is placed, or it may incorporate other sensors and hardware, such as is the case with system 700. Most of the components for this sampling system are contained within enclosure 1307, which houses the air intake valves 1302 through which samples are taken, a means for interconnecting the valves via one common manifold 1303, a sensor suite 1304 comprising one or more sensors, a central vacuum pump system 1306, and a controller 1305.

The system works by sequencing air samples through air intake valves 1302 which air samples are thereby drawn through sensor suite 1304 via the negative pressure established by pump 1306. As an air sample from a given room or location passes through sensor suite 1304 air parameters sensed by 1304 are monitored and typically recorded by controller 1305. Controller 1305 is also responsible for sequencing air intake valves 1302. Many types of tubing 1301 have been used in systems like 1300, including tubing made from polyethylene, Plexco®, Teflon, rigid stainless steel pipe, and other materials. However, the benefits realized by system 700 by using inventive tubing, e.g., 200,300, 400,500 equally apply to systems such as 1300, as well as other multipoint air sampling strategies.

The inventive tubing, e.g., 200,300,400,500 in system 1300, for example, provides a flexible, easy to install, and low cost tubing with good particulate transport properties along with low adsorption and absorption properties. The tubing, e.g., 200,300,400,500 enables the system 1300 to remotely monitor low-level concentrations of volatile organic compounds, while also simultaneously providing capabilities to remotely monitor particulates at locations throughout the building within which system 1300 is installed. Using the inventive tubing in the system 1300 would, for example, enable the use of a photoionization detector (for ppb-level VOC monitoring) and a particle counter within sensor suite 1304.

In addition, air monitoring systems, such as system 1300, can also benefit from the structured assemblies 600,900, and 1100 to provide power and communications, along with signal connections to discrete devices and sensors that may be located within various rooms and other monitoring locations throughout system 1300. This provides a convenient way to expand the capabilities of systems like 1300, while minimizing installation costs. Using such assemblies 600, 900, and 1100 also enables distance measurements to be made using sense lines 609 in order to optimize the sequencing of air samples from various rooms and other monitoring locations throughout system 1300. System 1300 may also utilize heater element 901 to improve particle transport efficiency and to help prevent condensation of certain VOC's or other gases, including water that could condense out of the air while they are being transported from the rooms and other locations in system 1300 to the sensor suite 1304. Also, the principles that were described for actively or passively controlling charge on the tubing's inner liner 652 in system 700/1000 in order to promote particle transport in air samples, applies to systems such as 1300 as well.

The present invention provides a tubing structure that is well suited to transport "packets" of air in an air sampling system. The tubing includes a metallic inner layer and an optional outer jacket that provides efficient transport of particulate matter through the tubing and relatively little absorption and off-gassing for many air components of interest.

Figure 14B:
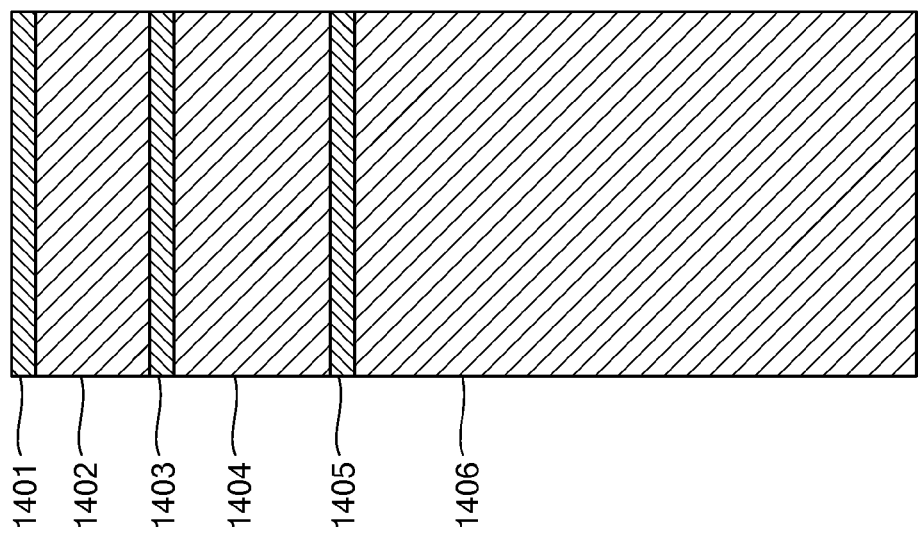
FIG. 14B is an exaggerated partial length-wise cut away view of the tubing of FIG. 14A.
Figure 14A:
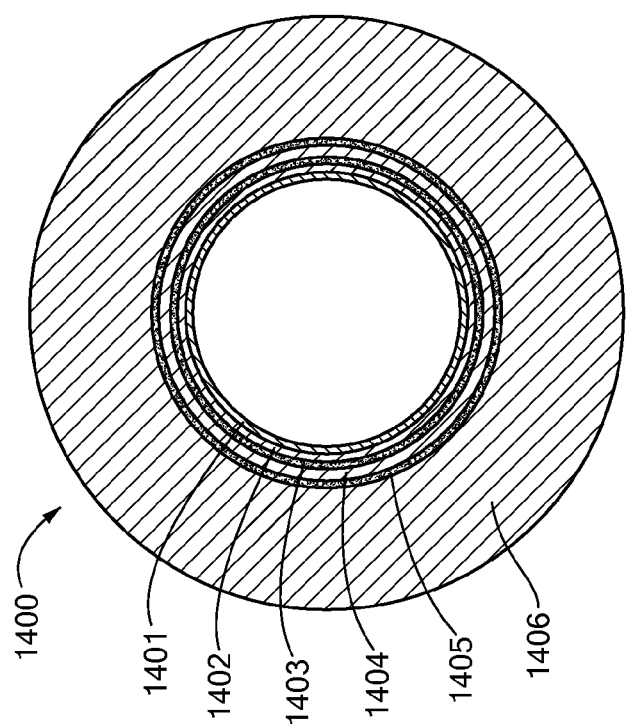
FIG. 14A is an exaggerated longitudinal cross-sectional view of a tubing having an electrically conductive liner in accordance with the present invention.

FIG. 14A shows an exemplary embodiment of an assembly 1400 in exaggerated cross section including a metal lined tubing utilizing a substrate onto which a metal foil is adhered. FIG. 14B shows an exaggerated cross sectional unfolded view of the tubing assembly 1400 of FIG. 14A. The assembly 1400 includes a metal liner 1402 that is metallized with a suitable material such as 316 stainless steel. In one embodiment, the metal liner 1402 is adhered to a suitable substrate 1404 by adhesive 1403; the substrate 1404 is in turn adhered to outer jacket 1406 by a suitable further adhesive 1405.

In an exemplary embodiment, the liner 1402 includes aluminum foil having a thickness ranging from about 0.0005 inch to about 0.005 inch. In one particular embodiment, the thickness is about 0.001 inch. In an exemplary embodiment, the metallized layer 1401 is 316 stainless steel ranging from about 100 to 1000 Angstroms in thickness, and in one embodiment the thickness is about 200 Angstroms. The adhesive layer 1403 is from 0.0001 inch to 0.002 inch in thickness and can be a curing-type of permanent adhesive chosen to be adhesively compatible with the materials used for 1402 and 1404. In an illustrative embodiment, the substrate layer 1404 is a polyamide film (such as Kapton®) ranging from about 0.0005 inch to about 0.003 inch with a thickness of about 0.001 inch in one embodiment that is gravure coated with a heat activated adhesive, that is used to adhere substrate 1404 to an extruded outer jacket 1406, which can be made of PVC.

In an alternative embodiment, the metal liner 1402 is made of aluminum that has an anhydrous aluminum oxide surface—at least on the surface forming the tubing's inner surface—(resulting in properties that are chemically the same as industrial sapphire), and the metallized layer 1401 is omitted.

In an another embodiment of the invention, the metal liner 1402 is made of a thin stainless steel foil having a thickness ranging from about 0.001 inches to about 0.0005 inch or less, and metallized layer 1401 is omitted. It is understood that other thicknesses for the metal liner are possible.

In another embodiment of the invention, metal liner 1402 is made of a thin nickel-plated copper foil. An exemplary range for a thickness of the nickel-plated copper foil is from about 0.001 inches to about 0.0005 inches or less. In an illustrative embodiment, the metallized layer 1401 is omitted.

In one embodiment, the foil liner 1402 and the adhesive 1403 are omitted, and the metallized layer 1401 is deposited directly onto the substrate layer 1404, which is made of Kapton® or other suitable plastic material.

Figure 9:
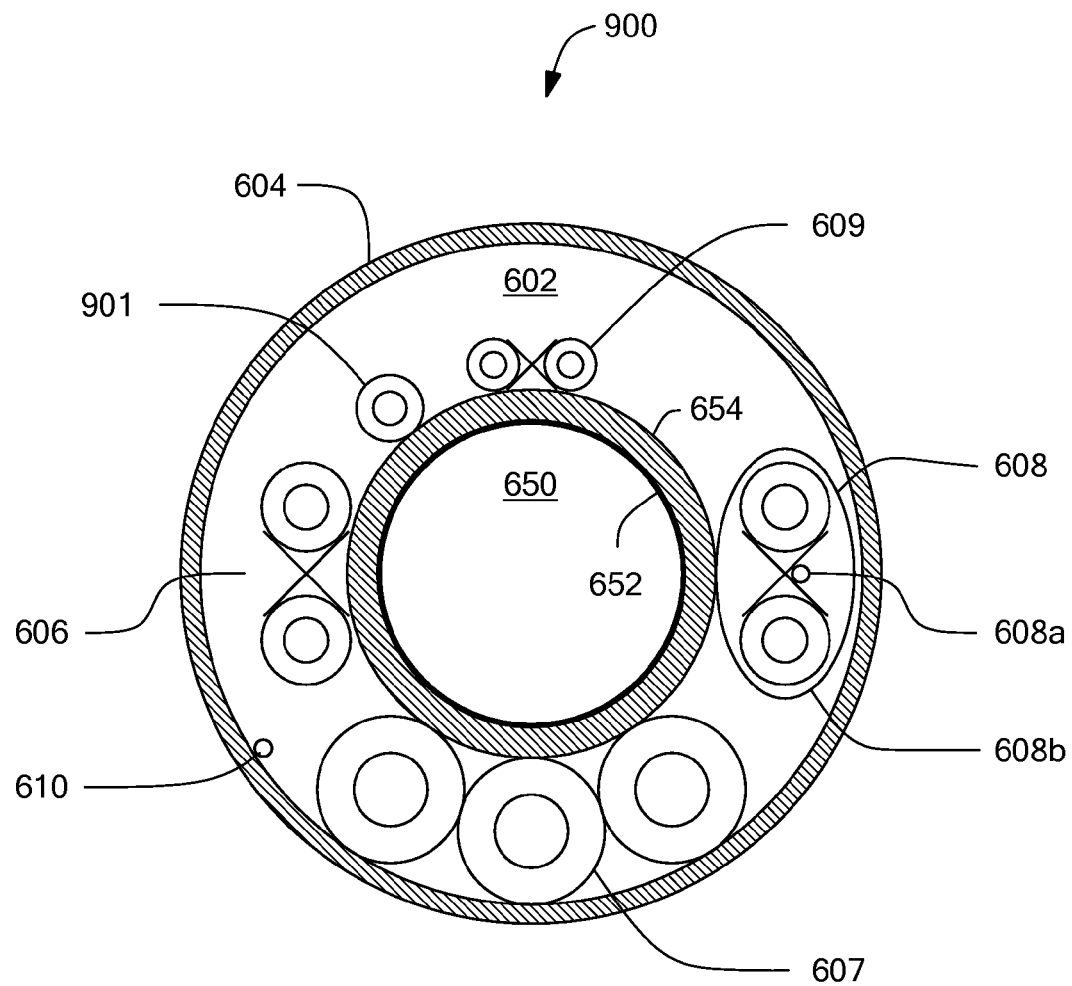
FIG. 9 is a cross-sectional view of a structured cable assembly including a resistive conductor.

The inventive tubing 1400 is well-suited for use in system 100 (FIG. 1) as tubing 105 as well as in star-configured systems 1300 (FIG. 13) as tubing 1301, providing a flexible, easy to install, and low cost tubing with good particulate transport properties along with low adsorption and absorption properties. In addition, inventive tubing 1400 may be incorporated within a structured assembly 600 (FIG. 6A) and 900 (FIG. 9) as tubing 650, so that it may be used in systems such as 700 (FIG. 7), 800 (FIG. 8), and 1000 (FIG. 10A). Inventive tubing 1400 may additionally be used as tubing 650 within structured assemblies 600 and 900 applied to system 1300 to provide power and communications, along with signal connections to discrete devices and sensors that may be located within various rooms and other monitoring locations throughout a building. In this way, tubing 1400/650 may be applied within an assembly 600 and 900 to facilitate electrical connections within 1300 that may, for example, be a refrigerant or other toxic gas monitoring system adapted to also support remote devices, such as temperature and other discrete sensors and devices, located at termination point 1308.

Figure 15:
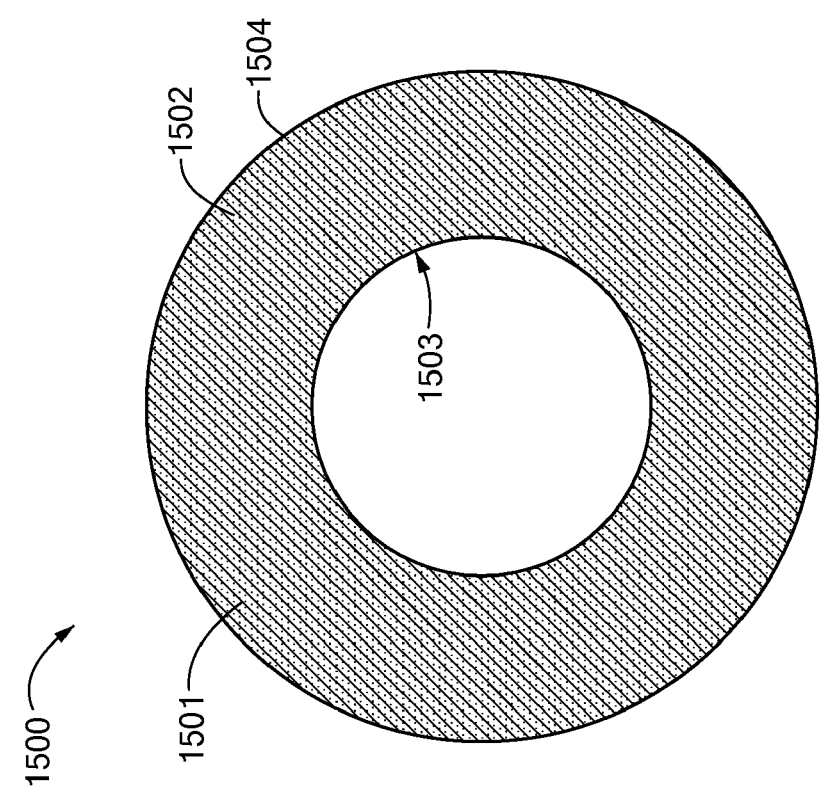
FIG. 15 is a cross-sectional view of a tubing embodiment having carbon based material in accordance with the present invention.

FIG. 15 shows tubing assembly 1500 having a suitable host material 1502 impregnated with carbon-based material 1501. In one embodiment, the carbon-based material 1501 is carbon black, which is an amorphous, powdered form of highly dispersed elemental carbon. To achieve a target volume resistivity in the range of 10 to 10,000 Ohm-centimeters, a loading of carbon black between 15 to 30% by weight is provided. In one embodiment, a loading percentage of about 20% by weight is used to obtain desired mechanical properties with a volume resistivity of about 1000 Ohm-centimeters.

Carbon black is used as a filler material in a wide variety of plastics to make a plastic composite with conductive properties to reduce static charges that can generate sparks and or dust pick-up. Typically, this increased conductivity is used for electrostatic or EMI shielding, or to reduce electrostatic discharge with sensitive electronics in normal or clean room environments. It is also used to transport flammable or volatile liquids or gases to prevent the possibility of igniting these materials from an electrostatic discharge. An example of this type of electrically conductive tubing material is carbon black filled PTFE tubing, part number 23478, from TexLoc Ltd. It is known that the volume resistivity may have some variation due to both the specific formulation of carbon black used, as well as the difficulties in getting an even distribution of carbon black in the filler material. This characteristic called dispersability indicates the ease with which the conductive carbon material can be wetted with the resin and subsequently de-agglomerated. This measure is independent of the plastic host material used to disperse the carbon black or other carbon based material. In addition to cost, a higher loading of carbon black negatively changes the physical properties of the host material, for example, making it stiffer and harder to extrude or mold.

In an exemplary embodiment, the carbon based material 1501 used as filler material includes carbon nanotubes. Carbon nanotubes are an allotrope of carbon that offers high conductivity, high durability, and is chemically inert, all of which are preferred properties for an air sampling tube.

Derived from spheroidal fullerenes ("Buckyballs"), carbon nanotubes (sometimes called "Buckytubes") are long and hollow arrays of hexagonal-pattern carbon atoms. They can be made with a single wall of carbon atoms in a form also know as single-wall nanotubes (SWNT) similar to a single layer of graphite rolled into a tube. This class of nanotube is typically 0.7 to about 2 nanometers in diameter and several hundred micrometers long with a typical diameter of about 1 nanometer. Another form of nanotubes is known as multi-wall nanotubes (MWNT), which are made with multiple concentric layers of carbon atoms to form thicker nanotubes. These nanotubes can be from about 3 to approximately 30 nanometers in diameter with similar lengths to SWNT with a typical diameter of about 10 nanometers. Carbon nanotubes can also have the resulting electronic structure of a true metal like copper or gold. They may be created, for example, by applying a direct-current arc discharge, typically from an arc welder, between two graphite electrodes in an inert atmosphere. One example of multi-wall carbon nanotubes are the FIBRIL™ Nanotubes manufactured by Hyperion Catalysis, Inc. which have a typical diameter of about 10 to 12 nanometers and have a typical structure employing about 8 layers or concentric shells of carbon atoms. An example of single-wall nanotubes are those manufactured by Carbon Nanotechnologies, Inc.

Carbon nanotubes have been used as a conductive additive mostly to polymer-based hosts in order to create antistatic and electromagnetic shielding and absorbing materials commonly used in the packaging of electronics. One of the advantages that carbon nanotubes have as an additive in these applications, is that the amount of nanotubes required to give a certain level of conductivity in a polymer based host is much less than that for other conductive filler materials. This is due to the nanotube's extremely high length to width aspect ratio equal to many thousands plus their high electrical conductivity. Carbon nanotubes can also self assemble into ropes of tens to hundreds of aligned tubes to make even longer conductive pathways further reducing the amount of filler required. By being able to use a small amount of filler material, cost is reduced plus the mechanical properties such as stiffness are minimally impacted creating the conductive tubing 1500 that is flexible and easy to install into buildings. For example, to achieve conductivity in the range of 10 to 10,000 Ohm-centimeters the host material 1502 is loaded with a range of about 1% to 5% by weight of carbon nanotubes 1501 with some variation being determined by how well the carbon nanotubes can be evenly distributed in the host polymeric material. In one embodiment, about 3.5% of carbon nanotubes by weight is used to achieve bulk conductivity levels of about 10 Ohm-centimeters.

Another advantage of carbon nanotubes for use as filler material 1501 in conductive tubing 1500 that will be used for sampling VOCs, is that the potential for adsorption and desorption is minimized. This is due to both the relative inertness of the nanotubes as well as the fact that nanotubes are less prone to sloughing off into the air stream or presenting much surface area to the airflow. This is because of the relatively small diameter of the nanotubes (approaching the size range of the polymer chains in the host matrix 1502), their flexibility, and the superior "wetting" and intertwining or mixing of the nanotubes with the long polymer chains of the host material 1502 to effectively form a polymer blend.

In another embodiment, the carbon based material 1501 used as filler material includes carbon nanofibers. Nanofibers are often formed in similar processes to what are used to make carbon nanotubes. Effectively, carbon nanofibers can start as multi-wall carbon nanotubes but are grown with many more layers or carbon atom shells to create tubes or fibers that are between approximately 70 to 300 nanometers in diameter and can be up to several hundred micrometers long. A manufacturer of nanofibers is Pyrograph Products, Inc. and their Pyrograph III nanofibers, which are about 70 to 200 nanometers wide and about 50 to 100 micrometers long. Nanofibers can be less expensive than carbon nanotubes but require higher filler loading such as in the range of 5 to 15% by weight.

In another embodiment, the filler material 1501 used in the host material 1502 includes carbon fibers. Commercially available structural carbon fibers are derived either from polyacrylonitrile (PAN) fibers or a special petroleum pitch (Pitch fibers) and then may be further chopped or milled for use as an electrical conductivity polymer additive. PAN and Pitch derived carbon fibers are also used as a continuous reinforcement for structural applications. Carbon fibers are typically in the range of 5 or 10 micrometers wide and 60 to 300 micrometers long.

To get the same 10 to 10,000 Ohm-centimeter previously mentioned, requires loading of between 10 to 20% by weight which puts them between carbon black and carbon nanofibers in required loading performance.

In another embodiment, the filler material 1501 used in the host material 1502 includes graphite particles. Graphite is an allotrope of carbon with conductive properties. An example of a graphite filler material for plastic is Conductograph graphite powder from SGL technologies. Graphite can be used in either a powder form, made into fibers to reduce the filler loading percentage, or combined with Nickel to form a Nickel graphite compound such as made by Westaim Ambeon of Alberta, Canada. Graphite is also relatively inert chemically which is advantageous for use in tubing to measure VOCs. Using a Nickel graphite compound filler for example to reach the 10 to 10,000 Ohm centimeter volume resistivity mentioned earlier requires loading of about 40 to 50% by weight of the graphite compound, putting it at the high end of loading requirements versus the carbon-based materials discussed above.

The desirable chemical properties of the host material 1502 include flexibility as well as being an inert material that does not off-gas, or act as a sorbent material for any of the desired air parameters that are to be measured with the air sampling system such as VOCs. This ability to have low levels of sorption or desorption is desirable for accurate air sampling of many gases or vapors. For example, Dekoron™ low density polyethylene (LDPE) plastic commonly used for pneumatic tubing is both an adsorbent and absorbent of VOCs and is not a suitable host material if VOCs are to be measured. Similarly, if humidity is of interest the material needs to be hydrophobic so the tubing does not adsorb/absorb or desorb water vapor which could compromise the accuracy of low humidity or dew point temperature measurements. For example, for measuring low dew points, some types of nylon are not preferred since they can introduce severe lag into the measurement system due to the long potential delay in the establishment of an equilibrium position, potentially taking days to reach a final equilibrium value. It is also helpful for the host material to be impermeable to gases such CO2, CO and other gases or vapors of interest. Furthermore certain host materials 1502 may be incompatible with some types of air parameter sensors. For example, the Mixed Metal Oxide Semiconductor family of sensors that are used to detect a range of compounds such as VOCs, CO, ozone, and hydrocarbons can be poisoned or seriously affected by contact with silicone vapors. Good corrosion resistance is also desirable so air contaminated with certain corrosive gases or agents does not affect the lining of the sampling tube assembly which could release particles or affect the surface finish of the inner wall. Finally, the host material 1502 should have properties such that the carbon based filler material can be easily mixed and compounded into the host mixture to produce a blended mixture that has an even dispersion of the filler material for good surface conductivity.

The fluoropolymer PVDF (polyvinylidene fluoride) also known as Kynar® is an exemplary choice of the host material 1502 having a good combination of extremely low adsorption/desorption, corrosion resistance, impermeability to water vapor and gases, flexibility, corrosion resistance and compatibility with carbon based filler materials. It is also less expensive than some other host materials having similar characteristics, and its moderate melting temperature makes it easier and less expensive to extrude or mold. Other suitable host materials include, but are not limited to other fluoropolymer resin plastics such as PTFE, FEP, PFA, PEEK, EFTE, CTFE, ECTFE, MFA, THV, and PEI. Non fluoropolymer resin plastics can also be suitable host materials based on having the desired levels of the above physical, material, and chemical properties.

The embodiments of tubing 1500 are well-suited for use in system 100 (FIG. 1) as tubing 105 as well as in star-configured systems 1300 (FIG. 13) as tubing 1301, providing a flexible, easy to install, and low cost tubing with good particulate transport properties along with low adsorption and absorption properties to allow accurate measurement of gases, vapors or other air parameters. In addition, inventive tubing 1500 may be incorporated within a structured assembly 600 (FIG. 6A) and 900 (FIG. 9) as tubing 650, so that it may be used in systems such as 700 (FIG. 7), 800 (FIG. 8), and 1000 (FIG. 10A).

Because of the relatively simple construction of tubing 1500 (FIG. 15), its cross section can easily be made to contain a uniform distribution of carbon based filler material, providing a conductive path from the tube's inner surface 1503 to its outer surface 1504. This makes tubing 1500 highly suitable for use within structured cable assembly 1100 (FIG. 11), enabling charge that may develop on inner surface 1503 to conduct to the outer surface 1504 which, in this embodiment is in contact with shield 1101 that is also electrically connected to drain wire 1102, that is used to conduct charge from the tubing. This promotes good particle transport characteristics within the tubing 650/1500, as it helps to minimize particle drop out due to electrophoresis.

Inventive tubing 1500 may additionally be used as tubing 650 within structured assemblies 600 and 900 to provide power and communications, along with signal connections to discrete devices and sensors that may be located within various rooms and other monitoring locations throughout system 1300. In this way, tubing 1500/650 may be applied within an assembly 600 and 900 to facilitate electrical connections within multipoint sampling system 1300 that may, for example, be a refrigerant or other toxic gas monitoring system adapted to also support remote devices, such as temperature and other discrete sensors and devices, located at termination points 1308 (FIG. 13).

Figure 16:
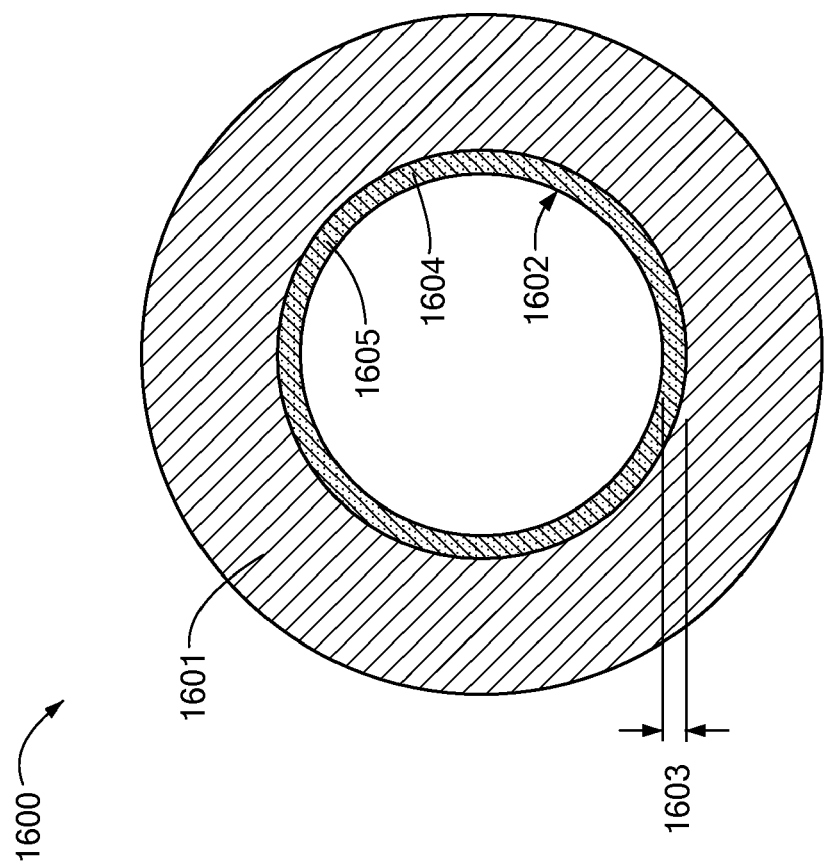
FIG. 16 is a cross-sectional view of a composite tubing embodiment having a jacket.

FIG. 16 is an illustration of embodiment of tubing 1600 that is a co-extrusion composed of a conductive composite inner layer 1602 that is over-extruded with a suitable jacket layer 1601. In one embodiment, inner layer 1602 includes a host material of polyvinylidene fluoride (PVDF) 1604, also known by the brand name Kynar®, that is impregnated with carbon-based material 1605. Other suitable host materials include, but are not limited to fluoropolymer resin plastics such as PTFE, FEP, PFA, PEEK, EFTE, CTFE, ECTFE, MFA, THV, and PEI.

The outer jacket layer 1601 may be composed of various plastics, depending on what can adequately bond to the host material 1604 of the inner layer 1602. In one embodiment, the outer jacket layer 1601 is composed of unfilled PVDF (no carbon based material) and the inner layer 1602 is composed of carbon nanotube impregnated PVDF. Other suitable inner layer filler materials include other carbon-based materials such as carbon black, carbon nanofibers, and/or carbon fiber. One advantage of the tubing embodiment 1600 of FIG. 16 is that its material cost is less than that of the tubing 1500 of FIG. 15 since, for a tube 1600 having a comparable cross section to that of 1500, less carbon-based material is required. This can be desirable since at present, carbon nanotubes, are far more expensive by weight than most plastics.

The tubing 1600 may be made to any practical dimensions to meet the needs of a particular application. However, it may be preferred that the outer diameter of the tubing 1600 be a standard size that can be supported by commercially available quick-connect style fittings, such as the John Guest Super Speedfit®. Although the tubing may be made to almost any size, two standard sizes for the tubing outer diameter are 5/16 inches and 3/8 inches. In one embodiment, where the outer diameter of the tubing 1600 is about 3/8 inches, the inner diameter will range from about 1/4 of an inch to about 5/16 of an inch. In an exemplary embodiment where the tubing 1600 outer diameter is about 5/16 of an inch, in its inner diameter is about 1/4 of an inch.

It is understood that the inner layer 1603 thickness may be any practical value to meet the needs of a particular embodiment. However, as discussed above, it may be beneficial to minimize the thickness 1603 of inner layer 1602 so as to reduce the overall cost of the tubing 1600. An exemplary thickness 1603 for the inner layer 1602 is about 0.010 inch with other suitable thicknesses ranging from about 0.005 inch to about 0.030 inch in thickness. It will be appreciated that it may be advantageous to make the tubing inner diameter compatible with standard barb fittings (1/4 inch, 5/16 inch, 6 millimeter), as that presents an alternative way to interconnect tubing pieces within a system. In addition, if the barb fittings are electrically conductive, such as brass or stainless steel fittings, an electrical connection between various section and components in the system can be effected, which can help to minimize charge buildup along lengths of tubing and therefore potentially promote better particle transport efficiency.

The embodiments of tubing 1600 are highly suited for use in system 100 as tubing 105 as well as in star-configured systems 1300 as tubing 1301, providing a flexible, easy to install, and low cost tubing with good particulate transport properties along with low adsorption and absorption properties. In addition, inventive tubing 1600 may be incorporated within a structured assembly 600 and 900 as tubing 650, so that it may be used in systems such as 700, 800, and 1000.

In one embodiment, the jacket layer 1601 is composed of plastic material that is impregnated with an electrically conductive material such as a finely divided metal such as stainless steel or another suitable material, such as carbon-black or another carbon based material. By making both the composite inner layer 1602 and jacket layer 1601 electrically conductive, the tubing 1600 is conductive throughout its cross section, allowing charge on the inner surface of the tube to conduct to the tube's outer surface. This embodiment of tubing 1600 may be applied as 650 to structured cable assembly 1100 (FIG. 11). In such a configuration, charge that may develop on the inner surface of the tube 1600/650 conducts to the tube's outer surface, which is in contact with shield 1101 that is also electrically connected to drain wire 1102 that is used to conduct charge away from the tubing. As discussed, this promotes good particle transport characteristics within the tubing 650/1600, as it helps to minimize particle drop out due to electrophoresis. The advantage of this approach over that of using tubing 1500 within assembly 1100 is that a lower cost conductive filler material with less critical requirements than that required for the inner layer 1603 can be used for the jacket layer 1601. Thus for a given tubing cross sectional area less of a more expensive conductive filler materials such as carbon nanotubes are required in order to make tubing that is conductive throughout its cross section.

Inventive tubing 1600 may additionally be used as tubing 650 within structured assemblies 600 and 900 to provide power and communications, along with signal connections to discrete devices and sensors that may be located within various rooms and other monitoring locations throughout system 1300. In this way, tubing 1600/650 may be applied within an assembly 600 and 900 to facilitate electrical connections within multipoint sampling system 1300 that may, for example, be a refrigerant or other toxic gas monitoring system adapted to also support remote devices, such as temperature and other discrete sensors and devices, located at termination points 1308.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An air sampling system, comprising:
    a sensor suite that measures at least one characteristic of an air sample;
    air intake valves for switching air samples; and
    tubing coupled to the air intake valves and a plurality of termination points from which air samples are obtained and transported via the tubing to the sensor suite, wherein at least a portion of the tubing includes an electrically conductive inner layer having carbon nanotubes in a host material, wherein the combination of the host material and the carbon nanotubes minimizes absorption, desorption and off-gassing for the air samples.

2. The system according to claim 1, wherein the tubing has no outer layer, only an inner layer encompasses the entire thickness of the tubing wall.

3. The system according to claim 1, wherein the tubing includes an outer layer that does not contain substantive amounts of carbon nanotubes.

4. The system according to claim 1, wherein the inner layer includes the host material loaded with between one and six percent by weight of carbon nanotubes.

5. The system according to claim 4, wherein the host material includes one or more of a fluoropolyner resin plastic.

6. The system according to claim 1, wherein the inner layer has a thickness in a range from about 0.005 inch to about 0.03 inch.

7. The system according to claim 1, wherein the sensor suite measures some level of information about the amount of particles in the air sample and one or more of a measure of VOCs, dew point, and carbon dioxide levels.

8. The system according to claim 1, further including securing at least one conductor to the tubing to provide one or more of signal, power, and communication.

9. The system according to claim 1, wherein the tubing is part of a structured cable assembly including two or more conductors.

10. An air sampling system, comprising:
a sensor suite including two or more air parameter sensors to measure multiple characteristics of an air sample; air intake valves for switching air samples; and
tubing coupled to the air intake valves and a plurality of termination points from which air samples are obtained and transported via the tubing to the sensor suite, wherein the tubing includes an electrically conductive inner layer comprising a host material that is loaded with at least one type of carbon based material, wherein a combination of the host material and the at least one type of carbon-based material minimizes absorption, desorption, and off-gassing for the air samples.

11. The system according to claim 10, wherein the carbon based material includes carbon black.

12. The system according to claim 10, wherein the carbon based material includes carbon nanofibers.

13. The system according to claim 10, wherein the carbon based material includes carbon fibers.

14. The system according to claim 10, wherein the carbon based material contains carbon single-wall nanotubes.

15. The system according to claim 10, wherein the carbon based material contains carbon multi-wall nanotubes.

16. The system according to claim 10, wherein the carbon based material contains graphite.

17. The system according to claim 10, wherein the tubing has no outer layer, only an inner layer encompasses the entire thickness of the tubing wall.

18. The system according to claim 10, wherein the tubing includes a nonconductive outer layer that does not contain substantive amounts of carbon based material.

19. The system according to claim 10 wherein the host material is made from a fluoropolymer resin plastic.

20. The system according to claim 19, wherein the fluoropolymer resin plastic is a PVDF based material.

21. The system according to claim 10, wherein the sensor suite measures some level of information about the amount of particles in the air sample along with one or more of a measure of VOCs, dew point, and carbon dioxide levels.

22. The system according to claim 10, further including securing at least one conductor to the tubing to provide one or more of signal, power, and communication.

23. The system according to claim 10, wherein the tubing is part of a structured cable assembly including two or more conductors.

* * * * *